United States Patent
Yoon

(10) Patent No.: US 10,736,592 B2
(45) Date of Patent: Aug. 11, 2020

(54) METHOD FOR PRODUCING COMPLEX REAL THREE-DIMENSIONAL IMAGES, AND SYSTEM FOR SAME

(71) Applicant: CATHOLIC KWANDONG UNIVERSITY INDUSTRY ACADEMIC COOPERATION FOUNDATION, Gangneung-Si (KR)

(72) Inventor: Cheesoon Yoon, Seoul (KR)

(73) Assignee: CATHOLIC KWANDONG UNIVERSITY INDUSTRY ACADEMIC COOPERATION FOUNDATION, Gangneung-Si (KR)

(*) Notice: Subject to any disclaimer, the term of this patent is extended or adjusted under 35 U.S.C. 154(b) by 649 days.

(21) Appl. No.: 14/655,387

(22) PCT Filed: Dec. 26, 2013

(86) PCT No.: PCT/KR2013/012232
§ 371 (c)(1),
(2) Date: Jun. 25, 2015

(87) PCT Pub. No.: WO2014/104767
PCT Pub. Date: Jul. 3, 2014

(65) Prior Publication Data
US 2015/0320513 A1   Nov. 12, 2015

(30) Foreign Application Priority Data

Dec. 26, 2012  (KR) .......................... 10-2012-0153032
Jun. 28, 2013  (KR) .......................... 10-2013-0075667
Dec. 26, 2013  (KR) .......................... 10-2013-0164216

(51) Int. Cl.
*A61B 6/00* (2006.01)
*G06T 7/00* (2017.01)
(Continued)

(52) U.S. Cl.
CPC .............. *A61B 6/487* (2013.01); *A61B 5/061* (2013.01); *A61B 6/022* (2013.01); *A61B 6/027* (2013.01);
(Continued)

(58) Field of Classification Search
CPC .................................................... A61B 6/487
See application file for complete search history.

(56) References Cited

U.S. PATENT DOCUMENTS 5,398,691 A * 3/1995 Martin ................. A61B 1/0052
600/437
5,999,840 A * 12/1999 Grimson ............... G06T 3/0068
600/424
(Continued)

FOREIGN PATENT DOCUMENTS

CN   102316817 A   1/2012
JP   2950340 B2    9/1999
(Continued)

OTHER PUBLICATIONS

International Search Report for International Application No. PCT/KR2013/012232, dated May 12, 2014 (7 pages).
(Continued)

*Primary Examiner* — Rochelle D Turchen
(74) *Attorney, Agent, or Firm* — Clark & Elbing LLP; Susan M. Michaud

(57) ABSTRACT

The present invention relates to a method for producing complex reality three-dimensional images and a system for same, the method comprising: (a) a step for determining first reality three-dimensional spatial coordinates for a three-dimensional image of a human body; (b) a step for determining second reality three-dimensional spatial coordinates for an image of an item of medical equipment; (c) a step for obtaining a three-dimensional image of the area surrounding
(Continued)

the medical equipment, from an imaging means in the medical equipment, and determining third reality three-dimensional spatial coordinates for said image; (d) a step for examining an image that is at the same coordinates in the three kinds of three-dimensional spatial coordinates; and (e) a step for producing a complex reality three-dimensional image by selecting the one image that is at the same coordinates, if there is one image at the same coordinates, or selecting the necessary image or images from among a plurality of images, if there are multiple images at the same coordinates.

39 Claims, 9 Drawing Sheets

(51) Int. Cl.
*A61B 6/02* (2006.01)
*A61B 5/06* (2006.01)
*A61B 90/00* (2016.01)
*A61B 34/20* (2016.01)

(52) U.S. Cl.
CPC ............ *G06T 7/0012* (2013.01); *A61B 6/503* (2013.01); *A61B 2034/2065* (2016.02); *A61B 2090/3966* (2016.02); *G06T 2207/10072* (2013.01); *G06T 2207/10121* (2013.01)

(56) References Cited

U.S. PATENT DOCUMENTS

| | | | |
|---|---|---|---|
| 7,697,972 B2* | 4/2010 | Verard | A61B 1/00071 |
| | | | 600/407 |
| 8,251,893 B2 | 8/2012 | Yamamoto et al. | |
| 2005/0113846 A1* | 5/2005 | Carson | A61F 2/461 |
| | | | 606/130 |
| 2007/0237290 A1* | 10/2007 | Mostafavi | A61B 6/025 |
| | | | 378/21 |
| 2008/0009829 A1* | 1/2008 | Ta | A61F 2/856 |
| | | | 604/509 |
| 2011/0270084 A1 | 11/2011 | Choi et al. | |
| 2012/0257049 A1* | 10/2012 | Schnell | G06T 11/001 |
| | | | 348/135 |
| 2013/0172670 A1* | 7/2013 | Levy | A61B 1/00105 |
| | | | 600/103 |

FOREIGN PATENT DOCUMENTS

| | | |
|---|---|---|
| JP | 2010-274044 A | 12/2010 |
| WO | WO-96/07144 A1 | 3/1996 |
| WO | WO-2008/093517 A1 | 8/2008 |

OTHER PUBLICATIONS

Office Action dated Dec. 8, 2017 for Chinese Patent Application No. 201380068009.X, Yoon, "Method for producing complex real three-dimensional images, and system for same," filed Dec. 26, 2013 (23 pages).

\* cited by examiner (a)

(b)

METHOD FOR PRODUCING COMPLEX REAL THREE-DIMENSIONAL IMAGES, AND SYSTEM FOR SAME

TECHNICAL FIELD

The present invention relates to a method for producing a complex reality three-dimensional image and a system for the same.

BACKGROUND ART

During operations in which a medical device is invasively or non-invasively inserted into the human body, a precise spatial location of the medical device inserted into the human body as well as precise spatial locations of human tissues is required in order to increase the success rate of surgery and prevent unexpected medical emergencies.

In the conventional medical technology, for the diagnosis and treatment of a patient, a medical device that enters the body of the patient is inserted without a precise location thereof after three dimensional images of the body of the patient are captured in advance using magnetic resonance imaging (MRI), computed tomography (CT), PET CT, gamma camera, or the like.

This medical technology has problems in that tissues of the patient body may be unnecessarily dissected and the undesired tissue dissection may cause fetal complications since three-dimensional spatial coordinates of the patient body are known through MRI or CT but three-dimensional coordinates of the medical device inserted into the patient body cannot be grasped in real time during operations.

In order to solve these problems, there is provided "a relative coordinate extracting device and a medical imaging device using the same (Korean Patent Publication No. 10-2012-0096729)" as a technology of obtaining spatial coordinates of the patient body during operations. This technology discloses that an image capturing device is installed in the patient body and relative coordinates of the image capturing device with respect to a target marker are calculated, but has problems in that accurate spatial coordinates of the patient cannot be recognized in a region of the human body in which the image capturing device is installed, and in cases where a prompt surgical operation needs to be done due to the critical condition of the patient, the installation of the image capturing device and the coordinate analysis may cause waste of so called golden time.

In addition, an example of a technology for analyzing a three-dimensional image of a particular subject is "a three-dimensional shape measurement method and a three dimensional measurement system (Korean Patent Publication No: 10-2012-0090964". This technology discloses that coordinate values representing a three-dimensional shape of a first part of a subject to be measured and coordinate values representing a three-dimensional shape of a second part of the subject are converted into coordinate values based upon a reference coordinate system identified by marks, and the coordinate values after the conversion are synthesized, so that entire three-dimensional shape data of the subject are obtained. This technology is somewhat similar to a proposal of the present invention with respect to three-dimensional spatial coordination of a medical device. However, this technology requires a separate light source and a reference coordination system, which cannot be used at the time of separate operations, and thus has a decisive problem in that this equipment cannot be placed in an operation room.

Moreover, this technology merely recognizes the three-dimensional shape of a particular subject, but cannot describe the coordinates of the particular subject in a three-dimensional space. Therefore, this technology cannot be applied to the three-dimensional space coordinates of the medical device. Recently, it is a trend to perform operations and procedures using various images, and here, the excellence of performance cannot be provided since the operations or procedures are performed while different images are determined through different imaging devices.

Throughout the entire specification, many cited documents and patent documents are referenced and their citations are represented. The disclosures of cited documents and patent documents are entirely incorporated by reference into the present specification, and the level of the technical field within which the present invention falls, and details of the present invention are explained more clearly.

DETAILED DESCRIPTION OF THE INVENTION

Technical Problem

The present inventors have endeavored to solve the problems of the conventional art. As a result, the present inventors have developed a novel method capable of accurately finding a three-dimensional position of a medical device used in a procedure, by allowing three-dimensional spatial coordinates of the human body and three-dimensional spatial coordinates of the medical device to coincide with each other to integrate different kinds of images of the human body. According to the present invention, a reality three-dimensional image capable of grasping an actual procedure in real time in a procedure place can be produced.

Therefore, the present invention has been made in view of the above-mentioned problems, and an aspect of the present invention is to provide a method for producing a complex reality three-dimensional image.

Another aspect of the present invention is to provide a system for producing a complex reality three-dimensional image.

Other purposes and advantages of the present invention will become clarified by the following examples, claims, and drawings.

Technical Solution

In accordance with an aspect of the present invention, there is provided a method for producing a complex reality three-dimensional image, the method including:

(a) determining first reality three-dimensional spatial coordinates of a three-dimensional image of the human body obtained before a medical device is applied to a subject;

(b) determining second reality three-dimensional spatial coordinates of an image of the medical device applied to the subject, the medical device including an imaging unit;

(c) obtaining a three-dimensional image of the periphery of the medical device from the imaging unit of the medical device, and determining third reality three-dimensional spatial coordinates of the obtained image, the first reality three-dimensional spatial coordinates, the second reality three-dimensional spatial coordinates, and the third reality three-dimensional spatial coordinates being determined by using the same coordinate system;

(d) examining images on the same coordinates in the three three-dimensional spatial coordinates by using the first reality three-dimensional spatial coordinates, the second reality three-dimensional spatial coordinates, and the third reality three-dimensional spatial coordinates; and (e) producing a complex reality three-dimensional image by selecting, if one image is on the same coordinates, the one image, and selecting, if multiple images are on the same coordinates, necessary image(s) from the multiple images.

The present inventors have endeavored to solve the problems of the conventional art. As a result, the present inventors have developed a novel method capable of accurately grasping a three-dimensional position of a medical device used in a procedure, by allowing three-dimensional spatial coordinates of the human body and three-dimensional spatial coordinates of the medical device to coincide with each other and integrating different kinds of images of the human body. According to the present invention, a reality three-dimensional image capable of grasping an actual procedure in real time in a procedure place can be produced.

The present invention is directed to a complex reality three-dimensional image, and provides a feature of producing a single three-dimensional image by incorporating different images.

The images incorporated herein are a three-dimensional image of the human body, a three-dimensional image of the medical device, and a three-dimensional image of the periphery of the medical device (e.g., an image obtained by the image medical device). Preferably, the images incorporated herein are a three-dimensional image of the human body, a three-dimensional image of the medical device, and a three-dimensional image of the periphery of the medical device, and an image linked with signals of the human body or an image obtained by an image medical device. As used herein to refer to the three-dimensional image, the term "complex" refers to the incorporation of the different images into one image. As used herein to refer to the three-dimensional image, the term "reality" refers to showing an actual situation, in which a procedure is performed, in real time through the produced image. As used herein to refer to the three-dimensional spatial coordinates, the term "reality" refers to three-dimensional coordinates in a space or environment in which a procedure is performed.

The present invention has been described by the method for producing a complex reality three-dimensional image, but the present invention may be described by a method for unifying spatial coordinates of a three-dimensional image of the human body and spatial coordinates of a three-dimensional image of the medical device.

According to the present invention, in a space other than a space in which a procedure (e.g., an operation) is performed, spatial coordinates of a three-dimensional image obtained by scanning the human body through an imaging equipment are secured before a medical device is applied to a subject, and in the space in which the procedure is performed, three-dimensional spatial coordinates of a particular part of the human body are calculated by using various imaging methods, for example, X-ray fluoroscopy. The calculated three-dimensional spatial coordinates of the particular part are allowed to coincide with the coordinates of the particular part on the previously secured three-dimensional spatial coordinates of the human body, thereby obtaining first reality three-dimensional spatial coordinates of the three-dimensional image of the human body, which is a subject of the procedure. As for the medical device, a two-dimensional image of the medical device is secured by various image methods, for example, X-ray fluoroscopy, and then, second reality three-dimensional spatial coordinates of the medical device (including, e.g., a medical unit for working and a medical imaging unit) based on the distance relationship among the medical device, an X-ray light source, and an X-ray detector. Third three-dimensional spatial coordinates of a three-dimensional image obtained by the medical imaging unit are determined using the three-dimensional spatial coordinates of the medical device. Then, the first reality three-dimensional spatial coordinates of the three-dimensional image of the human body, the second reality three-dimensional spatial coordinates of the image of the medical device, and the third reality three-dimensional spatial coordinates of the three-dimensional image obtained by the medical imaging unit are incorporated to reconstitute a necessary image. Thus, the present invention can provide accuracy and convenience of the procedure.

According to an embodiment of the present invention, the first reality three-dimensional spatial coordinates, the second reality three-dimensional spatial coordinates, and the third reality three-dimensional spatial coordinates may be on an orthogonal coordinate system.

According to an embodiment of the present invention, the same coordinate system used to determine the first reality three-dimensional spatial coordinates, the second reality three-dimensional spatial coordinates, and the third reality three-dimensional spatial coordinates may be set based on an operation table on which the medical device is applied to the subject.

According to an embodiment of the present invention, the three-dimensional image of the human body used in step (a) may be an X-ray fluoroscopy image, a computed tomography (CT) image, a magnetic resonance imaging (MRI) image, a positron emission tomography (PET) image, a PET/CT image, a PET/MRI image, a radioisotope imaging (RI) image, an ultrasonography image, or a complex image thereof.

According to an embodiment of the present invention, the first reality three-dimensional spatial coordinates and the second reality three-dimensional spatial coordinates may be determined using electromagnetic radiation. The electromagnetic radiation is X-ray radiation or radiofrequency electromagnetic radiation, and particularly X-ray radiation.

According to an embodiment of the present invention, the first reality three-dimensional spatial coordinates and the second reality three-dimensional spatial coordinates may be determined using X-ray fluoroscopy.

According to an embodiment of the present invention, the first reality three-dimensional spatial coordinates and the second reality three-dimensional spatial coordinates may be determined using mono-plan fluoroscopy, bi-plan fluoroscopy, or multi-plan fluoroscopy.

According to an embodiment of the present invention, the first reality three-dimensional spatial coordinates of step (a) may be determined using three-dimensional spatial coordinates of the three-dimensional image of the human body obtained before the medical device is applied to the subject and reality three-dimensional spatial coordinates of a particular part of the subject human body.

According to an embodiment of the present invention, step (a) may include the following sub-steps of: (a-1) irradiating X-rays toward the particular part of the human body of the subject using a first X-ray light source; (a-2) detecting an X-ray fluoroscopy image of the human body by the first X-ray light source, using a first X-ray detector; (a-3) irradiating X-rays toward the particular part of the human body to cross the X-rays by the first X-ray light source, using a second X-ray light source; (a-4) detecting an X-ray fluoroscopy image of the human body by the second X-ray light source, using a second X-ray detector; and (a-5) determining the first reality three-dimensional spatial coordinates of the three-dimensional image of the human body by using the human body images detected by the first X-ray detector and the second X-ray detector.

According to an embodiment of the present invention, sub-step (a-5) may include: (a-5-1) determining three-dimensional spatial coordinates of the three-dimensional image of the particular part of the human body positioned between the first X-ray light source and the first X-ray detector, by using physical three-dimensional coordinate information of the first X-ray light source and the first X-ray detector, distance information therebetween, and size information of the particular part of the human body detected by the first X-ray detector, and determining three-dimensional spatial coordinates of the three-dimensional image of the particular part of the human body positioned between the second X-ray light source and the second X-ray detector, by using physical three-dimensional coordinate information of the second X-ray light source and the second X-ray detector, distance information therebetween, and size information of the particular portion of the human body detected by the second X-ray detector; (a-5-2) determining three-dimensional spatial coordinates of the particular part of the human body, by using the three-dimensional spatial coordinates of the three-dimensional image of the particular part of the human body positioned between the first X-ray light source and the first X-ray detector and the three-dimensional spatial coordinates of the three-dimensional image of the particular part of the human body positioned between the second X-ray light source and the second X-ray detector; and (a-5-3) allowing the three-dimensional spatial coordinates of the particular part of the human body to coincide with the three-dimensional spatial coordinates of the three-dimensional image of the human body of step (a) to determine the first reality three-dimensional spatial coordinates of the three-dimensional image of the human body.

According to an embodiment of the present invention, the medical device may include an identification part for recognizing the position of the medical device. Since the entire three-dimensional shape of the medical device shows a relative position based on the identification part, a three-dimensional image of the medical device is implemented by using the identification part in a step of implementing a complex reality image.

According to an embodiment of the present invention, the identification part may include at least one of: (i) at least one sphere-shaped identification part, (ii) at least one ring-shaped identification part, (iii) an identification part including a ring and at least one marker indicating a specific site of the ring, (iv) an identification part including at least one pair of rings, (v) an identification part including at least one pair of rings and at least one marker indicating a specific site of the rings, or (vi) an identification part including markers respectively indicating three differentiated points.

Particularly, the three points of (vi) the identification part are differentiated by using markers with different images, indicating the respective points, or indicating the points using ends of linear markers having differentiated images or intersection points of the markers.

According to an embodiment of the present invention, the identification part may include at least one pair of rings and at least one marker. Here, the pair of rings are mounted on the medical device at different positions, and the at least one marker is attached to a position (one side of the ring) at which the position of the ring is capable of being indicated.

According to an embodiment of the present invention, the at least one pair of rings may have different imaging characteristics. The term "different imaging characteristics" refers to some characteristics (e.g., position, thickness, shape, and radiation transmittance) that make images be differentiately shown. For example, the rings with different thicknesses are differentiately shown through X-ray fluoroscopy.

According to an embodiment of the present invention, in cases where the number of markers is two or more, the markers may have different imaging characteristics (e.g., position, thickness, shape, length, and radiation transmittance). According to a more specific embodiment, the two or more makers have different lengths, and thus different images are calculated to give different imaging characteristics.

According to an embodiment of the present invention, the second reality three-dimensional spatial coordinates may be determined using one or two or more X-ray fluoroscopy images, and step (b) may include the following sub-steps of: (b-1) irradiating X-rays toward the medical device using an X-ray light source; (b-2) detecting an X-ray fluoroscopy image of the medical device by the X-ray light source, by using an X-ray detector; and (b-3) determining the second reality three-dimensional spatial coordinates of the image of the medical device, by using the through-position of the identification part, which is seen through on the X-ray fluoroscopy image.

According to an embodiment of the present invention, in sub-step (b-3), the second reality three-dimensional spatial coordinates of the image of the medical device and three-dimensional spatial coordinates of the marker may be determined by using the through-position of the identification part, which is seen through on the X-ray fluoroscopy image, thereby grasping the relative position of an internal portion of the medical device from the three-dimensional spatial coordinates of the marker.

According to an embodiment of the present invention, sub-step (b-3) may be performed using three-dimensional position information of the identification part, or three-dimensional position information and dimension information (e.g., diameters of rings, distance between rings, and a shape of the ring attached on the medical device). More specifically, in sub-step (b-3), the second reality three-dimensional spatial coordinates of the image of the medical device are determined by using physical three-dimensional coordinate information of an X-ray light source and an X-ray detector, distance information therebetween, size information of the medical device detected by the X-ray detector, a diameter of the ring, and the distance between the rings.

According to an embodiment of the present invention, the medical device may include a radio wave reflector. According to an embodiment of the present invention, step (b) may include the following sub-steps of: (b-1) generating a first microwave toward the radio wave reflector using a first microwave generator; (b-2) generating a second microwave toward the radio wave reflector using a second microwave generator; (b-3), after sub-steps (b-1) and (b-2), receiving the first and second microwaves reflected from the radio wave reflector; and (b-4) determining the second reality three-dimensional spatial coordinates of the image of the medical device by using information of the received first and second microwaves.

According to an embodiment of the present invention, the imaging unit included in the medical device may include a plurality of cameras, and here, the three-dimensional image of the periphery of the medical device is obtained using the plurality of cameras in step (c). According to a more specific embodiment, the camera as the imaging unit may include an identification part, and more specifically, a pair of rings and a marker attached to one side of each of the rings, respectively, as the identification part.

According to an embodiment of the present invention, the imaging unit may be an ultrasonic probe, and here, the three-dimensional image of the periphery of the medical device is obtained using the ultrasonic probe in step (c). According to a more specific embodiment, the ultrasonic probe as the imaging unit may include an identification part, and more specifically, a pair of rings, a marker attached to one side of each of the rings, and a scan line, as the identification part.

According to an embodiment of the present invention, the three-dimensional image of the human body of step (a) and the three-dimensional image of the periphery of the medical device of step (c) may be different kinds of images.

According to an embodiment of the present invention, the image of the medical device and the three-dimensional image of the periphery of the medical device, which are on the same coordinates and selected in step (e) may be images at the same time point.

According to an embodiment of the present invention, the method of the present invention may further include a step of determining a three-dimensional image of a periodic-mobility human body part (e.g., heart), which has periodic mobility and generates signals (e.g., electrocardiogram, blood pressure, organ pressure, and abdominal pressure) linked with the periodic mobility, and fourth reality spatial coordinates thereof, and here, step (d) may be performed by using the first reality three-dimensional spatial coordinates, the second reality three-dimensional spatial coordinates, the third reality three-dimensional spatial coordinates, and the fourth reality spatial coordinates.

In accordance with another aspect of the present invention, there is provided

A system for producing a complex reality three-dimensional image, the system including:

(a) a first process for calculating first reality three-dimensional spatial coordinates of a three-dimensional image of the human body obtained before a medical device is applied to a subject; (ii) second reality three-dimensional spatial coordinates of an image of the medical device applied to the subject; and (iii) third reality three-dimensional spatial coordinates of a three-dimensional image of the periphery of the medical device, by using the same coordinate system; and (b) a second processor for examining images on the same coordinates in the three three-dimensional spatial coordinates, by using the first reality three-dimensional spatial coordinates, the second reality three-dimensional spatial, and the third reality three-dimensional spatial, and then, selecting, if one image is on the same coordinates, the one image, and selecting, if a plurality of images are on the same coordinates, necessary image(s) from the plurality of images, to produce a complex reality three-dimensional image.

The system of the present invention is for implementing the foregoing method of the present invention, and descriptions of overlapping contents therebetween are omitted to avoid excessive complication of the present specification.

According to an embodiment of the present invention, the system may further include an X-ray fluoroscopy imaging device, a computed tomography (CT) imaging device, a magnetic resonance imaging (MRI) imaging device, a positron emission tomography (PET) imaging device, a PET/CT imaging device, a PET/MRI imaging device, a radioisotope imaging (RI) imaging device, or an ultrasonography imaging device, for obtaining the three-dimensional image of the human body.

According to an embodiment of the present invention, the system further include an X-ray fluoroscopy imaging device or a radiofrequency electromagnetic radiation device for obtaining the first reality three-dimensional spatial coordinates and the second reality three-dimensional spatial coordinates.

According to an embodiment of the present invention, the system may further include a medical device, and the medical device may include an identification part for recognizing the position of the medical device.

According to an embodiment of the present invention, the medical device used in the present invention may include an imaging unit.

Advantageous Effects

Features and advantages of the present invention are summarized as follows:

(a) According to the present invention, an image capable of showing a three-dimensional movement of the medical device in real time in a three-dimensional image of the human body, which is obtained by allowing spatial coordinates of the human body in a place, where a medical practice is performed, to coincide with coordinates of a previously secured three-dimensional image of the human body and a three-dimensional image obtained from an imaging medical device on the place, can be produced.

(b) According to the present invention, the space of the medical device inserted into the human body can be recognized by grasping and coordinating the three-dimensional space of the medical device such that the previously secured three-dimensional image of the human body is allowed to coincide with a space location of the human body in the place where a medical practice is performed.

(c) According to the present invention, the three-dimensional space of the medical device can be recognized in real time through X-ray scans employed in the operation place.

(d) A precise operation can be performed through the medical device by recognizing three-dimensional coordinates of the medical device and the human body and then incorporating these coordinates.

(e) Since three-dimensional spatial coordinates of the medical device and the human body can be accurately recognized using X-ray light sources, microwaves, ultrasonography images, and 3D cameras, unnecessary dissection of internal organs of the patient and unexpected medical accidents can be prevented based on the accurate location of the human body and the medical device.

(f) Since the spatial coordinates of the medical device can be recognized through an X-ray scanner, which is necessarily used in the operation place, unnecessary external equipments need not be delivered into the operation place.

(g) Since the medical device operates inside the human body by allowing accurate three-dimensional spatial coordinates of the medical device to coincide with three-dimensional coordinates of the human body, a more precise and safer operation can be performed.

(h) Since the three-dimensional spatial coordinates of the human body, the three-dimensional spatial coordinates of the medical device, and the three-dimensional spatial coordinates of images of the human body and the medical device captured by an imaging medical device are combined to display the three-dimensional image, a more precise operation can be performed.

BRIEF DESCRIPTION OF THE DRAWINGS

In FIG. 8, when a straight light connecting points E and F is extended and the intersection points of the straight line and the images of the respective rings are G, H, I, and J, theses points are formed by passing the X-rays projected from the X-ray light source P through the center axis of the medical device including the rings. Here, points on the rings through which the X-ray pass are G', H', I', and J'.

MODE FOR CARRYING OUT THE INVENTION

Figure 1:
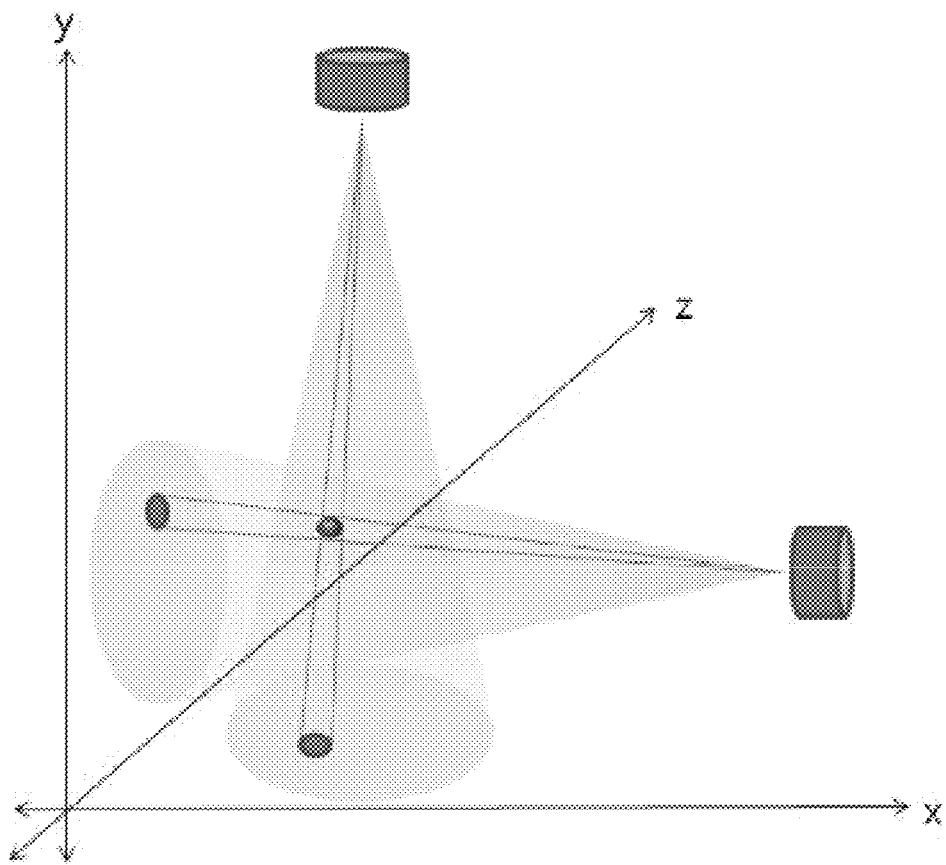
FIG. 1 is a view showing that X-rays are irradiated to a subject (a medical device) using a plurality of X-ray light sources.

The method and system for producing a complex reality three-dimensional image by incorporating spatial coordinates of the human body and a medical device, according to the present invention, can be variously modified, and may have several embodiments, and thus particular examples will be illustrated on the drawings, and detailed descriptions will be set forth. However, it shall be noted that it is not intended to limit the present invention to specific exemplary embodiments but intended to cover all the modifications, equivalents, or substitutions belonging to the technical idea and technical scope of the present invention.

Hereinafter, the method for producing a complex reality three-dimensional image of the present invention will be described with reference to drawings.

Step (a): Determining First Reality Three-Dimensional Spatial Coordinates of Three-Dimensional Image of Human Body According to the present invention, first reality three-dimensional spatial coordinates of a three-dimensional image of the human body, which is obtained before a medical device is applied to a subject, are determined.

The method for producing a complex reality three-dimensional image according to the present invention is carried out by obtaining first reality three-dimensional spatial coordinates of a three-dimensional image of the body of a subject (specifically, a human being, more specifically, a human patient) and second reality three-dimensional coordinates of an image of a medical device, respectively, and then allowing these three-dimensional spatial coordinates to coincide with each other.

The three-dimensional image of the human body obtained before the medical device is applied to the subject, which is used in the present invention, is obtained through various imaging equipments. The human body is scanned by an appropriate imaging equipment, thereby producing a three-dimensional image. The three-dimensional image of the human body, certainly, includes images of internal organs and bones as well as the skin.

According to an embodiment of the present invention, the three-dimensional image of the human body is an X-ray fluoroscopy image, a computed tomography (CT) image, a magnetic resonance imaging (MRI) image, a positron emission tomography (PET) image, a PET/CT image, a PET/MRI image, a radioisotope imaging (RI) image, an ultrasonography image, or a complex image thereof. According to a specific embodiment, a CT image or an MRI image is preferable.

The three-dimensional image of the human body may be one image obtained from the imaging equipment. Selectively, the three-dimensional image of the human body may be a complex image made by combining multiple images.

The first reality three-dimensional spatial coordinates may be determined using various electromagnetic rays, specifically, X-rays or high-frequency electromagnetic rays, and more specifically, X-rays.

In cases where the first reality three-dimensional spatial coordinates are determined using X-rays, the first reality three-dimensional spatial coordinates may be determined using X-ray fluoroscopy (mono-plan fluoroscopy, bi-plan fluoroscopy, or multi-plan fluoroscopy).

The first reality three-dimensional spatial coordinates of the three-dimensional image of the human body in step(a) may be determined by using the three-dimensional coordinates of the three-dimensional image of the human body obtained before the medical device is applied to the subject and reality three-dimensional spatial coordinates of a particular part of the subject human body. Alternatively, the three-dimensional spatial coordinates of the three-dimensional image of the human body may be directly determined without using the reality three-dimensional spatial coordinates of the particular part of the human body. For example, in the current procedure practice, an equipment for obtaining the three-dimensional image of the human body is installed on an operation table, and the three-dimensional image of the human body is obtained directly from a patient present on the operation table, thereby determining the reality three-dimensional spatial coordinates of the three-dimensional image of the human body. Alternatively, the reality three-dimensional spatial coordinates may be determined using the three-dimensional image obtained from the operation table and a three-dimensional image obtained from outside the operation table.

The reason is that, it is very effective to calculate and use reality three-dimensional spatial coordinates of a three-dimensional image obtained from CT scans or the like using X-ray fluoroscopy since the three-dimensional image of the human body from CT or MRI scans is obtained using a contrast agent, and thus has a different image quality from an image obtained from X-ray fluoroscopy without a contrast agent, and the contrast agent cannot be continuously used during an operating procedure.

The X-ray fluoroscopy may be performed in various manners. Specifically, the determining of the first reality three-dimensional spatial coordinates includes the following steps of: (a-1) irradiating X-rays toward the particular part of the human body of the subject using a first X-ray light source; (a-2) detecting an X-ray fluoroscopy image of the human body by the first X-ray light source, using a first X-ray detector; (a-3) irradiating X-rays toward the particular part of the human body to cross the X-rays by the first X-ray light source, using a second X-ray light source; (a-4) detecting an X-ray fluoroscopy image of the human body by the second X-ray light source, using a second X-ray detector; and (a-5) determining first reality three-dimensional spatial coordinates of the three-dimensional image of the human body by using the human body images detected by the first X-ray detector and the second X-ray detector.

Here, sub-step (a-5) includes: (a-5-1) determining three-dimensional spatial coordinates of the three-dimensional image of the particular part of the human body positioned between the first X-ray light source and the first X-ray detector, by using physical three-dimensional coordinate information of the first X-ray light source and the first X-ray detector, distance information therebetween, and size information of the particular part of the human body detected by the first X-ray detector, and determining three-dimensional spatial coordinates of the three-dimensional image of the particular part of the human body positioned between the second X-ray light source and the second X-ray detector, by using physical three-dimensional coordinate information of the second X-ray light source and the second X-ray detector, distance information therebetween, and size information of the particular portion of the human body detected by the second X-ray detector; (a-5-2) determining three-dimensional spatial coordinates of the particular part of the human body, by using the three-dimensional spatial coordinates of the three-dimensional image of the particular part of the human body positioned between the first X-ray light source and the first X-ray detector and the three-dimensional spatial coordinates of the three-dimensional image of the particular part of the human body positioned between the second X-ray light source and the second X-ray detector; and (a-5-3) allowing the three-dimensional spatial coordinates of the particular part of the human body to coincide with the three-dimensional spatial coordinates of the three-dimensional image of the human body of step (a) to determine the first reality three-dimensional spatial coordinates of the three-dimensional image of the human body.

The first reality three-dimensional spatial coordinates of the particular part of the human body, which can be well identified by X-ray fluoroscopy, are calculated by using a plurality of X-ray fluoroscopies, and reality three-dimensional spatial coordinates of the other parts are calculated based on the first reality three-dimensional spatial coordinates. The reality three-dimensional spatial coordinates calculated by using X-ray fluoroscopy can have a decreased error in cases where several parts of the human body are calculated. If the three-dimensional spatial coordinates of the three-dimensional image obtained by CT or MRI scans in an operating space are identical to the reality three-dimensional spatial coordinates, this process may be omitted.

The first reality three-dimensional spatial coordinates of the three-dimensional image of the human body, the second reality three-dimensional spatial coordinates, and the third reality three-dimensional spatial coordinates may be determined by using various coordinate systems capable of expressing three dimensions. For example, an orthogonal coordinate system may be used, but another coordinate system, for example, a spherical coordinate system or the like may be used as a reference coordinate system according to the environment in which the present invention is implemented, used equipments, and the like.

The same coordinate system is used in order to allow the first reality three-dimensional spatial coordinates, the second reality three-dimensional spatial coordinates, and the third reality three-dimensional spatial coordinates to coincide with one another, and in this case, various points of a space in which the procedure is performed may be used as references. Among the points, it is appropriate to use the operation table as a reference in the aspect of convenience.

For example, the coordinate system using the operation table as a reference may be constructed as follows. The operation table is horizontal, and the side at which the head of a patient is placed is an upper side, and the side of the leg of the patient is a lower end. When the left and right sides are set based on the observation from the lower end to the upper end, the x-, y-, and z-axes and origin point O are set as follows: The x-axis is a line which is parallel with the short axis of the operation table and horizontal while passing through the lower end of the operation table; the y-axis is a line which is vertical and meets the x-axis while passing through a point at which the X-ray detector or the X-ray light source is positioned at the left side as much as possible; and the z-axis, which is parallel with the long axis of the operation table and horizontal while passing through an intersection point of the x-axis and the y-axis.

According to an embodiment of the present invention, in cases where the operation table is used as the reference, the gradations on the operation table, which are helpful to set three-dimensional coordinates, are favorable in setting three-dimensional coordinates.

Step (b): Determining Second Reality Three-Dimensional Spatial Coordinates of Image of Medical Device Next, second reality three-dimensional spatial coordinates of an image of the medical device applied to the subject are determined. The medical device includes an imaging unit.

Apart from three-dimensional imaging of the human body and spatial coordinating of the three-dimensional image, the medical device is spatially coordinated.

Here, the medical device includes all medical devices which are in contact with an external part of the patient body or inserted into the human body. The medical devices used herein may be classified into two kinds, and one is an imaging medical device and the other is a functioning medical device. The functioning medical device is a tool for performing a procedure, such as scissors, a knife, and a needle, including a stent. Specifically, the medical device used herein includes various medical devices, such as an endoscope, an ultrasonography imaging device, and a surgical robot.

The caution here is that there is no order in time between the three-dimensional spatial coordination of the human body and the three-dimensional spatial coordination of the position of the medical device. Therefore, claims indicate the spatial coordination of the human body in step (a) and the spatial coordination of the medical device in step (b), but the spatial coordination of the medical device may be first performed, and this shall be construed to be included within the scope of a right of the present invention.

The three-dimensional spatial coordination of the human body and the three-dimensional spatial coordination of the medical device are performed in parallel and independently. However, in general, the operation or the like is performed after CT or MRI scans of the patient, and thus in practical, the three-dimensional imaging and the three-dimensional spatial coordination of the human body precede the three-dimensional spatial coordination of the medical device.

The spatial coordinates used herein need to be used in the same coordinate system, and the units thereof need to be the same as each other. The three-dimensional spatial coordinates of the medical device may be used in, for example, an orthogonal coordinate system.

The reality three-dimensional spatial coordinates of the human body and the medical device are obtained by, for example, X-ray fluoroscopy, and an ultrasonography imaging device or a 3D camera is additionally used to assist the spatial coordination by X-ray fluoroscopy.

In cases where the spatial coordinates are obtained by X-ray fluoroscopy, X-rays are continuously irradiated from a light source during the surgery of the patient. Therefore, the X-ray fluoroscopy makes it unnecessary to use separate medical devices, and thus is very economical.

The CT scanned image is not an image of the human body which varies in real time, and thus in order to supplement this, necessary images are obtained by using and combining 3D camera or ultrasonography images. The reference point for combining images may be based on the reality three-dimensional spatial coordinates at which the human body of the patient is positioned. The 3D camera or ultrasonography image is a three-dimensional image configured based on the reference point of each device, and thus when the reality three-dimensional spatial coordinates of the reference point are known, the three-dimensional spatial coordinates of the 3D camera or ultrasonography image of the human body or the medical device can be replaced with the reality three-dimensional spatial coordinates. The reality three-dimensional spatial coordinates of the medical device including an imaging device can be calculated from the three-dimensional spatial coordinates of the reference point of the imaging device by using X-ray fluoroscopy.

In cases where three-dimensional spatial coordinates are incorporated or allowed to coincide with each other, a plurality of various image coordinates are present in the identical spatial coordinates. Of these, the coordinates of necessary images are selected to reconstitute a three-dimensional image.

For example, in cases where a stent is inserted for the treatment of aortic aneurysm, a three-dimensional image of the human body obtained from CT scans using a contrast agent is used for the shape of the aorta, and a three-dimensional image calculated by X-ray fluoroscopy is used for the medical device including the stent. Here, the medical device including the stent is positioned in the aorta, and thus the coordinates of the medical device is included in the coordinates of the aorta, so that the coordinates of the medical device are expressed by the medical device, and the coordinates of the other aorta is expressed by the aorta.

As another example, in cases where the lung surgery is performed using a three-dimensional endoscope, the air gets out of the lung at the time of surgery, and thus the operation is performed while the volume of the lung is reduced, but the three-dimensional image from CT scans does not reflect the reduced volume. Therefore, the image from a 3D camera is used for the image of the lung with a reduced volume, and the three-dimensional image from CT is used for the image of a part that is not shown through the 3D camera.

As still another example, in cases where the heart valve surgery is performed using a catheter, the catheter arrives at the heat through the blood vessel, and here, the three-dimensional image of the catheter using X-ray fluoroscopy is used for the shape of the blood vessel in the three-dimensional image from CT. The movement of the heart valve is difficult to observe by X-ray fluoroscopy, and thus an ultrasonography image (two-dimensional or three-dimensional image) is used therefor. The detailed image of the catheter is difficult to grasp through the ultrasonography image, and thus a three-dimensional image using X-ray fluoroscopy is used therefor.

In addition, second reality three-dimensional spatial coordinates of the image of the medical device applied to the subject are determined.

The determination of the first reality three-dimensional spatial coordinates of the three-dimensional image of the human body and the second reality three-dimensional spatial coordinates of the image of the medical device will be described in detail by exemplifying X-ray fluoroscopy.

First, X-rays are irradiated toward a particular part of the human body (or a medical device) using a first X-ray light source $1a$. Thereafter, a first X-ray detector detects the X-rays that are irradiated from the first X-ray light source and passes through the particular part of the human body (or a medical device). In the same manner, X-rays are irradiated toward the particular part of the human body (or the medical device) using a second X-ray light source $1b$, and then a second X-ray detector detects the X-rays which are irradiated from the second X-ray light source and passes through the particular part of the human body (or the medical device). In this case, as shown in FIG. 1, the X-rays irradiated from the first X-ray light source and the second X-ray light source detect the same particular part of the human body (or the medical device), and cross each other.

Figure 3:
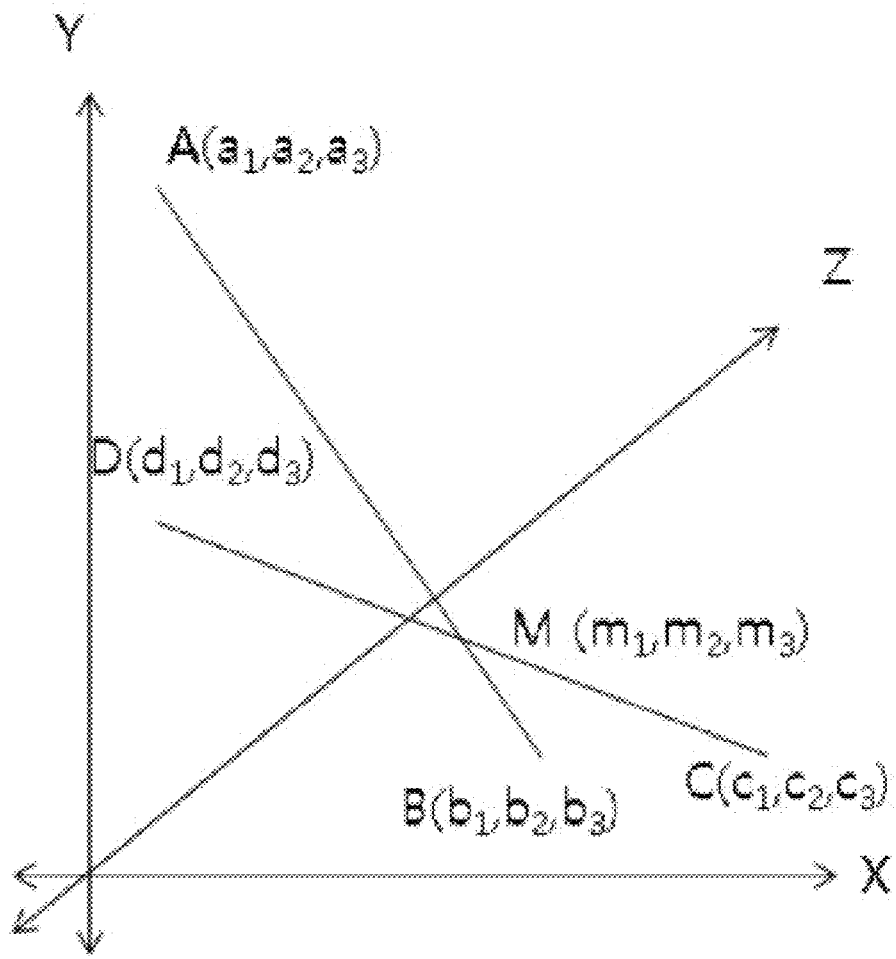
FIG. 3 is a view showing the plurality of X-ray light sources and an image of the subject in FIG. 1, and the projection of the subject on a three-dimensional plane.

The physical coordinate position of the first X-ray light source is information that is physically given in advance, and the physical coordinate position of the first X-ray detector is also information that is physically given in advance. In addition, the physical coordinate position of the second X-ray light source is information that is physically given in advance, and the physical coordinate position of the second X-ray detector is also information that is physically given in advance. If the particular part of the human body (or the medical device) is extremely small, the position thereof may be represented as a point at which lines meet each other, as shown in FIG. 3. In order to represent the detected particular part as a point, the particular part is a small region which is well detected by the X-ray, or the positional change of a region represented by the center point of the image needs to be small according to the detection angle. Here, the particular part of the human body is not limited to only a natural region of the human body, but includes an artificial material or natural material disposed inside or outside the human body.

In order to obtain the point at which lines meet each other in FIG. 3, real coordinates of the image on the detector needs to be obtained. When the X-ray detector is positioned in any space in the reality three-dimensional space, image A on the detector, which is generated by the X-rays, is shown in FIG. 2(a), and two-dimensional coordinates of the image on the detector are shown in FIG. 2(b).

The reality three-dimensional spatial coordinates of the position of the X-ray light source and the detector can be physically obtained using an X-ray fluoroscope installed on the operation table. Based on these, the reality three-dimensional spatial coordinates of the image on the detector may be obtained.

Figure 2:
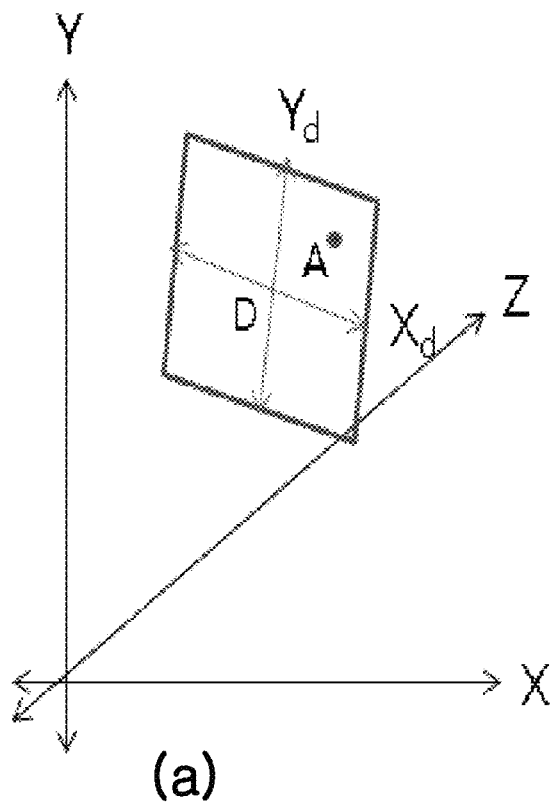
FIG. 2(a) shows the position of point A projected on a detector and the position of the detector in a three-dimensional space where three axes of an orthogonal coordinate system are plotted.
FIG. 2(b) shows point A on the detector on a two-dimensional plane of a rectangular coordinate system.
Figure 2:
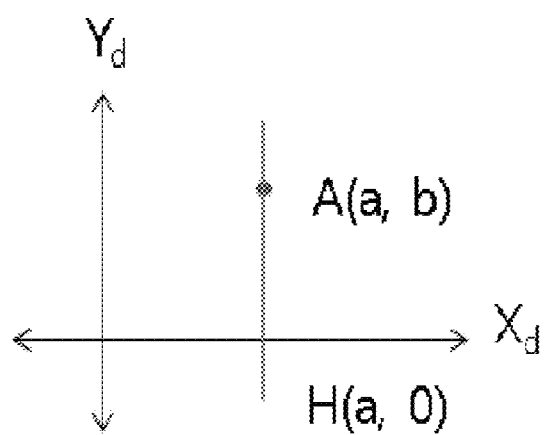

In FIG. 2, the center point D of the X-ray detector and the $X_d$ axis and the $Y_d$ axis constituting two-dimensional coordinates of the detector can be physically recognized. When the coordinates of point D are $(d_1, d_2, d_3)$, the vector of $X_d$ axis is $u'=(d, e, f)$, the vector of $Yd$ axis is $v'=(g, h, i)$, and coordinates of point A on the image generated on the detector are $(a, b)$, three-dimensional coordinates $(a_1, a_2, a_3)$ of point A can be calculated, and the method therefor is as follows.

Point A is positioned on the straight line which passes through point H and has vector v, and distanced from point H by an interval of b. Here, point H is distanced from point D by an interval of a, and positioned on the $X_d$ axis, and vector v is the same as the vector of $Y_d$.

If point A is $(h_1, h_2, h_3)$, $$a=\sqrt{(d_1-h_1)^2+(d_2-h_2)^2+(d_3-h_3)^2} \quad \text{Equation (1)}$$

Here, straight line $\overline{X}_d$ passes through point D and has $\vec{u}$, and thus the equation of $\overline{X}_d$ is given by $$\frac{(x-d_1)}{d} = \frac{(y-d_2)}{e} = \frac{(z-d_3)}{f}.$$

Since point H is on straight line $\overline{X}_d$, the put of the coordinates of point H is as follows:

$$\frac{(h_1-d_1)}{d} = \frac{(h_2-d_2)}{e} = \frac{(h_3-d_3)}{f}.$$

Therefore, $$h_2 = \frac{e}{d}(h_1-d_1) + d_2$$

$$h_3 = \frac{f}{d}(h_1-d_1) + d_3.$$

When these are put into equation (1), $$a = \sqrt{(h_1-d_1)^2 + \left\{\frac{e}{d}(h_1-d_1) + d_2 - d_2\right\}^2 + \left\{\frac{f}{d}(h_1-d_1) + d_3 - d_3\right\}^2}$$

$$a = \sqrt{(h_1-d_1)^2 + \left\{\frac{e}{d}(h_1-d_1)\right\}^2 + \left\{\frac{f}{d}(h_1-d_1)\right\}^2}$$

$$a = \sqrt{(h_1-d_1)^2 + \frac{e^2}{d^2}(h_1-d_1)^2 + \frac{f^2}{d^2}(h_1-d_1)^2}$$

$$a = \sqrt{\frac{d^2}{d^2}(h_1-d_1)^2 + \frac{e^2}{d^2}(h_1-d_1)^2 + \frac{f^2}{d^2}(h_1-d_1)^2}$$

$$a = (h_1-d_1)\sqrt{\frac{(d^2+e^2+f^2)}{d^2}}$$

$$h_1 - d_1 = \frac{ad}{\sqrt{d^2+e^2+f^2}}$$

$$h_1 = d_1 + \frac{d \times a}{\sqrt{d^2+e^2+f^2}}.$$

Solve it in the same manner, then $$h_2 = d_2 + \frac{e \times a}{\sqrt{d^2+e^2+f^2}}, \; h_3 = d_3 + \frac{f \times a}{\sqrt{d^2+e^2+f^2}}.$$

Thus, coordinates of point H $(h_1, h_2, h_3)$ are given by:

$$\left(d_1 + \frac{d \times a}{\sqrt{d^2+e^2+f^2}}, d_2 + \frac{e \times a}{\sqrt{d^2+e^2+f^2}}, d_3 + \frac{f \times a}{\sqrt{d^2+e^2+f^2}}\right).$$

Assume that this point is H $(h_1, h_2, h_3)$,

The straight line which passes through point H and has the vector of $Y_d$, that is, $v'(g, h, i)$, is given by:

$$\frac{(x-h_1)}{g} = \frac{(y-h_2)}{h} = \frac{(z-h_3)}{i}.$$

Since point A $(a_1, a_2, a_3)$ is on this straight line, the following equation is given:

$$\frac{(a_1-h_1)}{g} = \frac{(a_2-h_2)}{h} = \frac{(a_3-h_3)}{i} \rightarrow . \quad \text{Equation (2)}$$

Since the distance between point H and point A is b, the following equation is given:

$$b=\sqrt{(a_1-h_1)^2+(a_2-h_2)^2+(a_3-h_3)^2} \quad \text{Equation (3)}.$$

Equations (2) and (3) are summarized as follows:

$$a_1 = h_1 + \frac{g \times b}{\sqrt{g^2 + h^2 + i^2}}$$

$$a_2 = h_2 + \frac{h \times b}{\sqrt{g^2 + h^2 + i^2}}$$

$$a_3 = h_3 + \frac{i \times b}{\sqrt{g^2 + h^2 + i^2}}.$$

Then, put $$h_1 = d_1 + \frac{d \times a}{\sqrt{d^2 + e^2 + f^2}},$$

$$h_2 = d_2 + \frac{e \times a}{\sqrt{d^2 + e^2 + f^2}}, h_3 = d_3 + \frac{f \times a}{\sqrt{d^2 + e^2 + f^2}}$$

into the above equations:

$$a_1 = d_1 + \frac{d \times a}{\sqrt{d^2 + e^2 + f^2}} + \frac{g \times b}{\sqrt{g^2 + h^2 + i^2}}$$

$$a_2 = d_2 + \frac{e \times a}{\sqrt{d^2 + e^2 + f^2}} + \frac{h \times b}{\sqrt{g^2 + h^2 + i^2}}$$

$$a_3 = d_3 + \frac{f \times a}{\sqrt{d^2 + e^2 + f^2}} + \frac{i \times b}{\sqrt{g^2 + h^2 + i^2}}.$$

Therefore, when the center point D ($d_1$, $d_2$, $d_3$) of the radiation detector, vectors of reference lines of the detector, that is, $X_d$ and $Y_d$, $\vec{u}$, $\vec{v}$, and any point A (a, b) on the detector are known, three-dimensional coordinates of point A can be obtained.

After the reality three-dimensional spatial coordinates of any image on the detector are obtained as described above, coordinates of the intersection point in the three-dimensional space are obtained as shown in FIG. 3, and thus the coordinates will be coordinates of the particular part of the human body (or the medical device).

The coordinates are obtained as follows.

In FIG. 3, assuming that the image generated by shooting a subject M with an extremely small area from an X-ray light source A is represented by B and the image corresponding to a light source C is represented by D, for the sake of convenience, the equation of straight line $\overline{AB}$ through two points A and B is given by $$\frac{x - a_1}{a_1 - b_1} = \frac{y - a_2}{a_2 - b_2} = \frac{z - a_3}{a_3 - b_3}.$$

Assume that $\alpha_1 = a_1 - b_1$, $\alpha_2 = a_2 - b_2$, $\alpha_3 = a_3 - b_3$, then $$\frac{x - a_1}{\alpha_1} = \frac{y - a_2}{\alpha_2} = \frac{z - a_3}{\alpha_3}.$$

The equation of straight line $\overline{CD}$ through two points C and D is given by $$\frac{x - c_1}{\beta_1} = \frac{y - c_2}{\beta_2} = \frac{z - c_3}{\beta_3},$$

where $\beta_1 = c_1 - d_1$, $\beta_2 = c_2 - d_2$, and $\beta_3 = c_3 - d_3$.

Assume that the intersection point of straight lines $\overline{AB}$ and $\overline{CD}$ is M ($m_1$, $m_2$, $m_3$). Since point M is on straight lines $\overline{AB}$ and $\overline{CD}$, the following equations are given:

$$\frac{m_1 - a_1}{\alpha_1} = \frac{m_2 - a - 2}{\alpha_2} = \frac{m_3 - a_3}{\alpha_3} \rightarrow \quad \text{Equation (4)}$$

$$\frac{m_1 - c_1}{\beta_1} = \frac{m_2 - c_2}{\beta_2} = \frac{m_3 - c_3}{\beta_3} \rightarrow \quad \text{Equation (5)}$$

From equation (4), $m_2 = \frac{\alpha_2}{\alpha_1}(m_1 - a_1) + a_2$

From equation (5), $m_2 = \frac{\beta_2}{\beta_1}(m_1 - c_1) + c_2$ $$\frac{\alpha_2}{\alpha_1}(m_1 - a_1) + a_2 = \frac{\beta_2}{\beta_1}(m_1 - c_1) + c_2$$

$$\left(\frac{\alpha_2}{\alpha_1} - \frac{\beta_2}{\beta_1}\right)m_1 = \frac{\alpha_2}{\alpha_1} \times a_1 - \frac{\beta_2}{\beta_1}c_1 + c_2 - a_2$$

$$m_1 = \frac{\frac{\alpha_2}{\alpha_1} \times a_1 - \frac{\beta_2}{\beta_1}c_1 + c_2 - a_2}{\frac{\alpha_2}{\alpha_1} - \frac{\beta_2}{\beta_1}}.$$

In the same manner, $m_2$ and $m_3$ can be obtained.

As described above, radioscopy or a plurality of radioscopies used to obtain the reality three-dimensional coordinates of the particular part of the human body, and the obtained reality three-dimensional coordinates are allowed to coincide with three-dimensional coordinates of the three-dimensional image of CT or the like to obtain the reality three-dimensional spatial coordinates of the three-dimensional image of CT or the like.

Two or more fluoroscopies may be performed on the same particular part of the human body, and the more the fluoroscopies are performed, the smaller the error in the calculation of reality three-dimensional spatial coordinates.

In addition, as shown in FIG. 1, due to characteristics of X-rays spreading in all directions, the image of the particular part of the human body (or the medical device) on the detector will be enlarged as the particular part of the human body (or the medical device) is closer to the light source, and in contrast, the size of the image of the particular part of the human body (or the medical device) will be equal to an actual size of the particular part of the human body (or the medical device) as the particular part of the human body (or the medical device) is farther from the light source. The size of the image of the particular part of the human body (or the medical device) depending on the detected angle can be obtained from the three-dimensional image of CT or the like, and thus it can be calculated at which coordinates the particular part of the human body (or the medical device) is positioned between the first X-ray light source and the first detector and between the second X-ray and the second detector, by measuring the size of the image of the particular part of the human body (or the medical device). This can supplement the foregoing method in which the intersection point of two straight lines is calculated in the space to obtain the reality three-dimensional coordinates.

In the method of calculating the reality three-dimensional spatial coordinates of the medical device, the three-dimensional spatial coordinates of the medical device can be calculated more effectively when the mechanical shape and size of the medical device are known. In addition, the reality three-dimensional spatial coordinates of the medical device can also be calculated by merely a single time of X-ray fluoroscopy.

It is effective to mount an identification part on a predetermined part of the medical device and use the identification part rather than use the X-ray fluoroscopy while the entire shape and size of the medical device are known. The reason is that, in cases where the three-dimensional position of the identification part mounted on the medical device is found, the three-dimensional position of the entire medical device can be obtained by using the three-dimensional position of the identification part.

The identification part may have any shape, form, and structure as long as it is easily distinguishable from the human body, which is seen through by radiation fluoroscopy.

More particularly, the identification part is (i) at least one sphere-shaped identification part, (ii) at least one ring-shaped identification part, (iii) an identification part including a ring and at least one marker indicating a particular site of the ring, (iv) an identification part including at least one pair of rings, (v) an identification part including at least one pair of rings and at least one marker indicating a particular site of the rings, or (vi) an identification part including markers respectively indicating three differentiated points.

Of these identification parts, in a case of (vi) the identification part including markers respectively indicating three differentiated points, the three differentiated points are differentiated from one another by using makers with different images indicating the respective points or indicating the differentiated points using ends of linear markers with differentiated markers or the intersection points of the markers and the differentiated points.

According to an embodiment of the present invention, the identification part is composed of rings and markers, and the rings constitute at least one pair (the thicknesses of the rings are equal or different), and surround the medical device.

The two or more rings are spaced apart from each other on the medical device, and may be disposed at any position. For example, one ring may be positioned at one end of the medical device and the other ring may be positioned to be spaced apart from the end.

The identification may be formed of any material that has different radiation transmittance from the human body. For example, the identification part may be formed of a material having a high radiation transmittance.

According to an embodiment of the present invention, the rings may be positioned on the plane vertical with respect to the center axis of the medical device, or a plurality of markers may be mounted as needed. A plurality of markers may be mounted on the medical device, but ten or less markers are favorably disposed.

According to an embodiment of the present invention, the identification part includes two or more rings and one or more markers. The two or more rings are mounted on the medical device at different positions, and the one or more markers are mounted at positions at which the positions of the rings can be indicated. The marker is configured to indicate the specific site of the ring, and for example, the marker may be attached on one side of the ring, or the marker may indicate a specific portion of the ring even when the marker is disposed on the extension line of the linear marker without being attached to the ring at a distance.

Two or more rings may be disposed as needed, and preferably, the rings have different thicknesses so as to grasp the direction of the medical device. In addition, in cases where a marker capable of indicating the specific site of the ring is used, the relative position of an internal portion of the medical device can be grasped. The medical device may have a flexure portion, and here, in cases where two rings are disposed before and after the flexure portion, a three-dimensional flexible image can be obtained.

Figure 4:
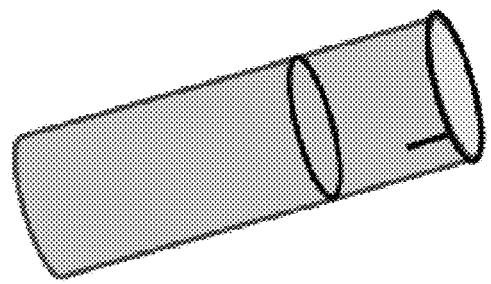
FIG. 4 is a conceptual perspective view showing a cylinder-shaped medical device attached with an identification part (rings and a marker).

FIG. 4 is a conceptual perspective view showing a cylinder-shaped medical device on which an identification part (rings and a marker) is attached. Here, for the sake of convenience of calculation, two rings are positioned on a surface of a cylinder which has the same center axis with the two rings, and on a plane vertical to the center axis, and the diameters of the two rings are equal. The following drawings are the same as above.

Figure 5:
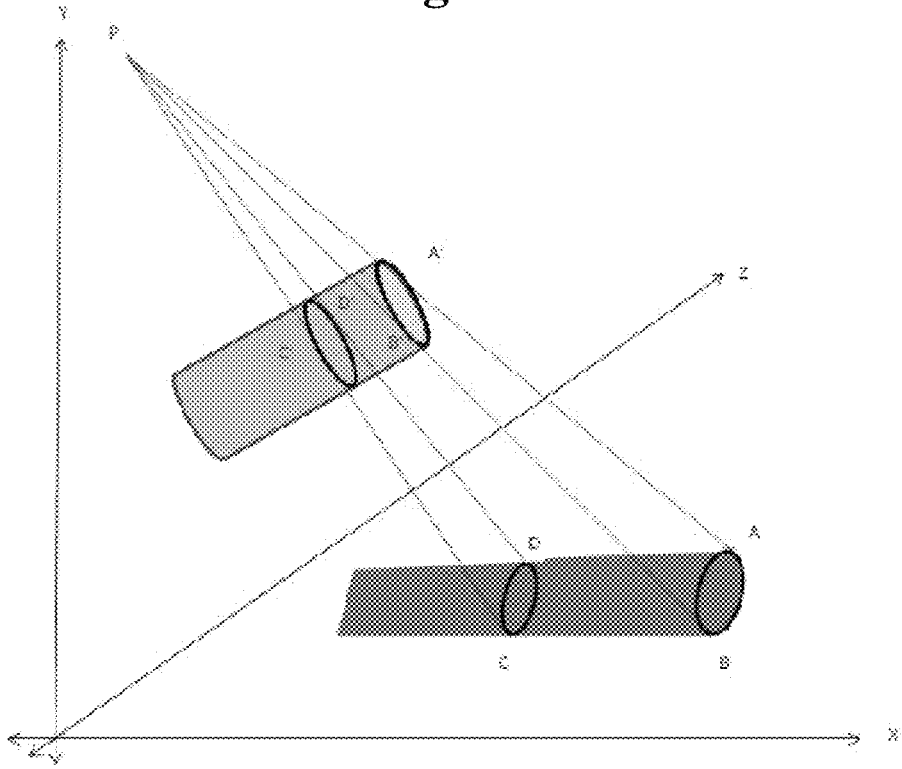
FIG. 5 is a view showing an image of a medical device on an X-ray detector and the projected medical device when X-rays are irradiated to the medical device from one X-ray light source P in a three-dimensional space (here, an identification part is omitted).
Figure 6:
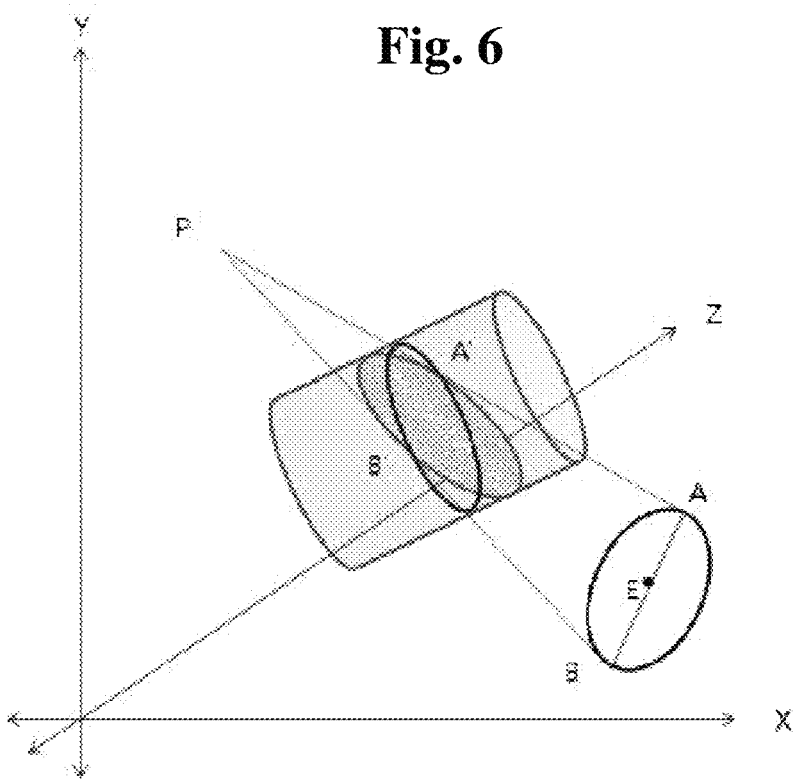
FIG. 6 is a three-dimensional plane view showing a portion (represented by hatching) of the medical device, through which X-rays pass from the X-ray light source P, wherein the portion forms an image of one ring and an image of straight line AB connecting edges of the ring image on the detector, in FIG. 5.
Figure 7:
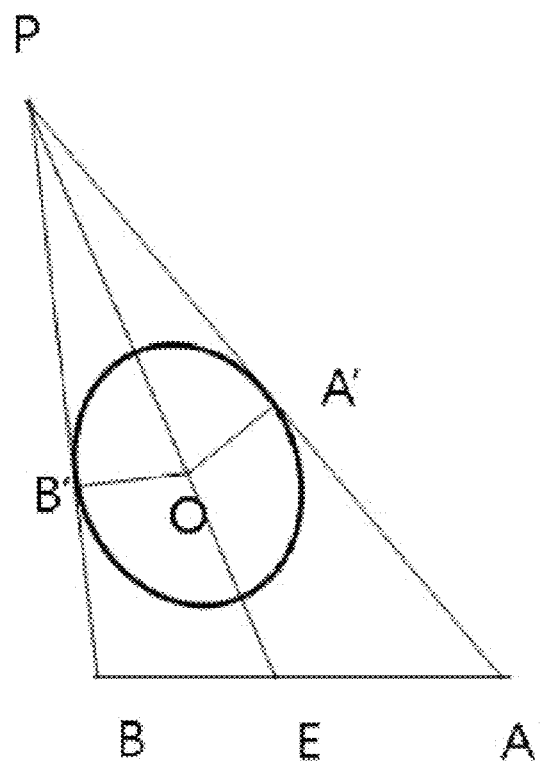
FIG. 7 is a view showing the X-ray light source P, the portion (represented by hatching) of the medical device through which X-rays pass, and straight line AB (virtual line) of the image on the detector, on a two-dimensional plane. The X-ray light source P, the portion of the medical device, and straight line AB are present on one plane in FIG. 6.

FIG. 5 shows an image obtained by passing radiation through a medical device attached with an identification part, which is disposed at any position, on a detector, which is disposed at any position, and the medical device, using a three-dimensional plane. The position of the image is on the detector. When the radiation is irradiated from an X-ray light source P, the radiation passes through the medical device to form an image on a surface of the detector as shown in FIG. 5. The radiation irradiated from the light source P passes through contact points A', B', C', and D' of two rings to form images A, B, C, and D corresponding to the contact points A', B', C', and D' on the surface of the detector. Therefore, points A', B', C', and D' are positioned on straight lines, $\overline{PA}$, $\overline{PB}$, $\overline{PC}$, and $\overline{PD}$. Hence, lines $\overline{PA}$, $\overline{PB}$, and $\overline{AB}$ are disposed on the same plane. As shown in FIG. 6, this plane is a face of the radiation which obliquely cuts and passes through the cylinder-shaped medical device from the X-ray light source P. In addition, FIG. 7 shows the foregoing plane through a two-dimensional view. As shown in FIG. 7, the cut shape of the cylinder is an ellipse, and the X-ray light source P is positioned on one axis of the ellipse having center point O. Straight lines $\overline{PA}$ and $\overline{PB}$ are tangential lines of the ellipse, which pass through point P, and pass through contact points A' and B'. In addition, assuming that the intersection point of straight line $\overline{PO}$ and straight line $\overline{AB}$ is point E, $\angle APE = \angle BPE$. Here, since coordinates of points P, A, and B are known, the intersection point of the straight line, which passes through point P and bisects $\angle APB$, and straight line $\overline{AB}$ can be calculated.

Assume that $\angle APE = \angle BPE = \alpha$, then area $S_1$ of triangle $\triangle APE$ is given by $S_1 = \frac{1}{2} \sin \alpha \overline{PA} \times \overline{PE}$, and area $S_2$ of $\triangle BPE$ is given by $S_2 = \frac{1}{2} \sin \alpha \overline{PB} \times \overline{PE}$. Thus, $S_1:S_2 = \frac{1}{2} \sin \alpha \overline{PA} \times \overline{PE} : \frac{1}{2} \sin \alpha \overline{PB} \times \overline{PE}$. Therefore, $S_1:S_2 = \overline{PA}:\overline{PB}$. Meanwhile, $\triangle APE$ and $\triangle BPE$ have the same height and different bottom sides, $S_1:S_2 = \overline{AE}:\overline{EB}$. Thus, $\overline{AE}:\overline{EB} = \overline{PA}:\overline{PB}$.

Figure 8:
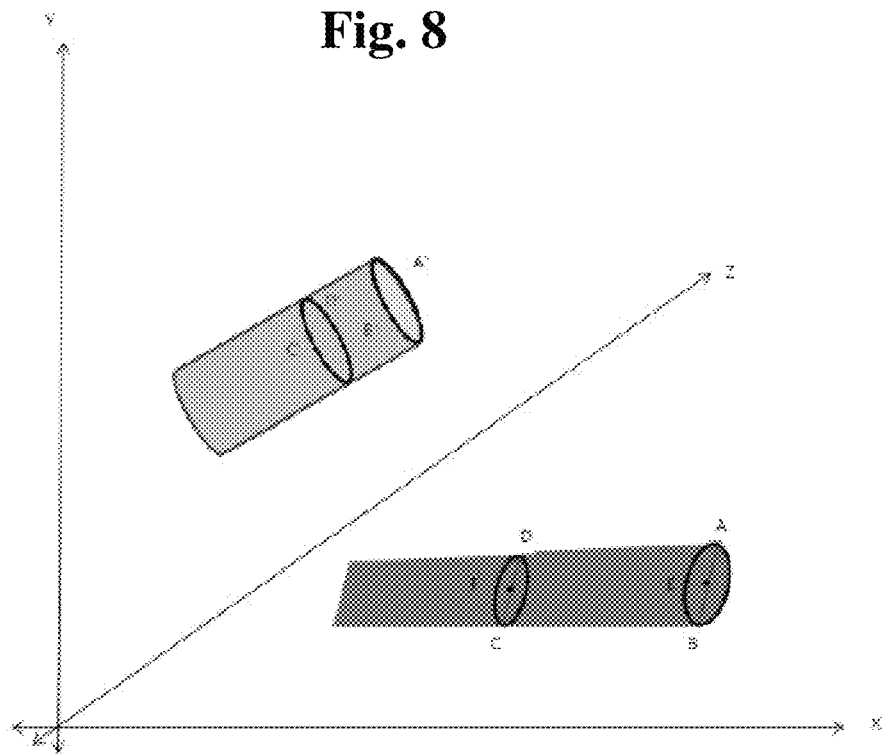
FIG. 8 is a view showing a medical device and an image of the medical device, when it is assumed that edge points of images of two rings are respectively A, B, C, and D, an intersection point of the straight line bisecting ∠APB and straight line AB is E, and an intersection point of the straight line bisecting ∠CPD and straight line CD is F.
Figure 9:
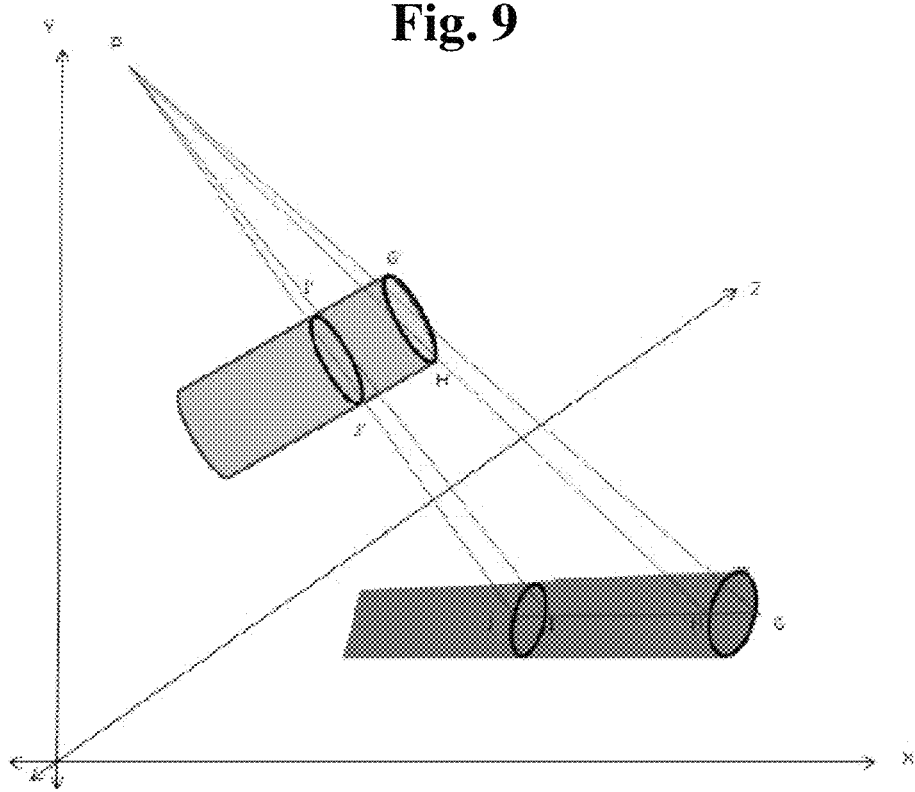
FIG. 9 is a view showing points G', H', I', and J' on a three-dimensional plane.
Figure 10:
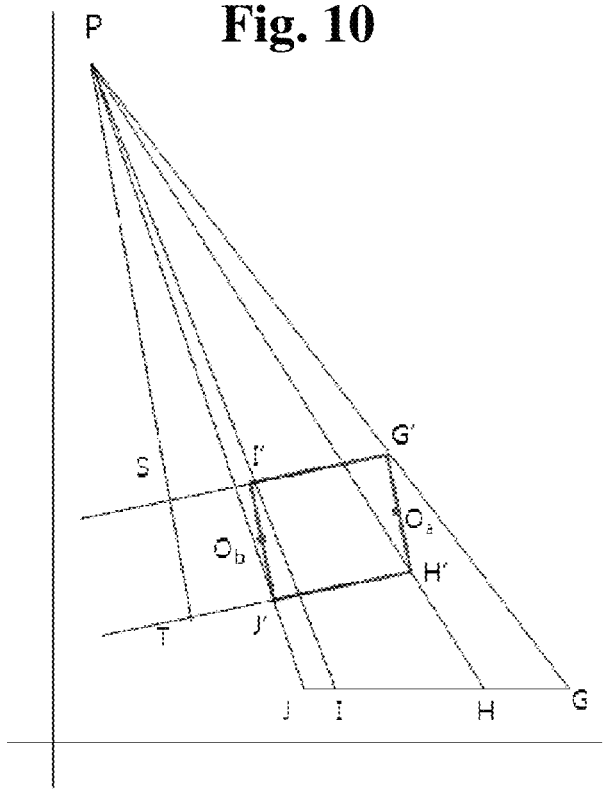
FIG. 10 shows a relationship among the points G, H, I, and J, which are formed by passing the X-rays through the center axis of the medical device, points G', H', I', and J' corresponding to these, and point P on a two-dimensional plane. Points G, H, I, and J, points G', H', I', and J', and point P are present on the same plane in FIG. 9. The medium point connecting points G' and H' is represented by $O_a$, and the medium point connecting points I' and J' is represented by $O_b$.

Assuming that the intersection points of line segments $\overline{AB}$ and $\overline{CD}$ and the lines which bisect $\angle APB$ and $\angle CPD$ are represented by points E and F, respectively, line segment $\overline{EF}$ is an image of the medical device obtained by passing the radiation irradiated from the X-ray light source P through the center axis of the cylinder-shaped medical device. The extension line of $\overline{EF}$ may also be the same as described above. As shown in FIGS. 8 to 10, assuming that the intersection points of the extension line of line segment EF and the images of one pair of rings are points G, H, I, and J, respectively, the radiation irradiated from the X-ray light source P passes through points G', H', I', and J' on the rings to form points G, H, I, and J on the image of the detector. Therefore, as shown in FIG. 10, points G', H', I', and J' are intersection points of a face including the center axis of the medical device, the X-ray light source P, and straight line $\overline{GJ}$ and one pair of rings mounted on the medical device.

Thus, points P, G, H, I, J, G', H', I', and J' are present on the same plane. FIG. 10 shows a two-dimensional view of this plane.

In FIG. 10, point P is an X-ray light source, and points G, H, I, and J are points of an image which is generated on the detector by passing the radiation irradiated from point P through points G', H', I', and J'.

Square G'H'I'J' is a longitudinal section of the cylinder, which is obtained by cutting the cylinder-shaped medical device between rings so as to include the center axis of the cylinder-shaped medical device. Therefore, square G'H'I'J' is a square shape. In addition, points G' and H' are on the ring and face each other based on the center of on the ring. In addition, points I' and J' are on the ring and face each other based on the center of the ring.

Therefore, the lengths of line segments $\overline{G'H'}$ and $\overline{I'J'}$ are the diameters of the rings, and the distance between line segments $\overline{G'I'}$ and $\overline{H'J'}$ is the distance between the rings.

Meanwhile, in order to find three-dimensional spatial coordinates of the cylinder-shaped medical device, three-dimensional spatial coordinates of the ring need to be obtained. In addition, when the center axis of the cylinder is obtained based on the three-dimensional spatial coordinates of the cylinder-shaped medical device, the excellence in the operation of the medical device can be secured. Assuming that the points that bisect $\overline{G'H'}$ and $\overline{I'J'}$ are represented by $O_a$ and $O_b$, the straight line connecting the two points is the center of the cylinder-shaped medical device (not shown in FIG. 10).

Therefore, when three-dimensional spatial coordinates of G', H', I', and J' are known, the three-dimensional spatial coordinates of the medical device may be obtained.

Since point P is the X-ray light source, and points G, H, I, and J are points of an image generated on the detector by passing the radiation irradiated from point P through points G', H', I', and J', three-dimensional spatial coordinates of points P, G, H, I, and J may be obtained by using the foregoing method.

Points G', H', I', and J' are positioned on straight lines $\overline{PG}$, $\overline{PH}$, $\overline{PI}$, and $\overline{PJ}$, and thus, when the distances thereof from point P, that is, the lengths of $\overline{PG'}$, $\overline{PH'}$, $\overline{PI'}$, and $\overline{PJ'}$ are known, the three-dimensional spatial coordinates of G', H', I', and J' may be calculated by using the equation of a straight line and the equation between two points.

As shown in FIG. 10, assume that intersection points of extension lines of line segments $\overline{G'I'}$ and $\overline{H'J'}$ and the normal line perpendicular to the extension lines from point P are designed as S and T, respectively; the length of $\overline{G'H'}$ and the length of $\overline{I'J'}$ are designated as R, the length of $\overline{G'I'}$ and the length of $\overline{H'J'}$ are designated as L, the length of $\overline{PS}$ is m, and the length of $\overline{I'S}$ and the length of $\overline{J'T}$ are n. Here, R is the diameter of the rings, and L is the distance between the rings.

These are expressed by:

$\overline{PS}=m$, $\overline{I'S}=\overline{J'T}=n$, $\angle PSG=\angle PTH'=\pi/2$ $\overline{G'H'}=\overline{I'J'}=R$, $\overline{G'I'}=\overline{H'J'}=L$ Therefore, $\overline{PG'}=\sqrt{(L+n)^2+m^2}$ $\overline{PH'}=\sqrt{(L+n)^2+(R+m)^2}$ $\overline{PI'}=\sqrt{n^2+m^2}$ $\overline{PJ'}=\sqrt{n^2+(R+m)^2}$.

Meanwhile, L and R are the distance between the rings and the diameter of the ring, and thus are previously known constants. Therefore, when m and n are found, the lengths of $\overline{PG'}$, $\overline{PH'}$, $\overline{PI'}$, and $\overline{PJ'}$ may be calculated.

Here, m and n are obtained as follows:

Assume that $\angle GPH=h$, $\angle HPI=i$, $\angle IPJ=j$, $\angle JPS=s$.

Then, $$\tan s = \frac{n}{(m+R)}$$

$$\tan(s+j) = \frac{n}{m}$$

$$\tan(s+j+i) = \frac{(L+n)}{(R+m)}$$

$$\tan(s+i+j+h) = \frac{(L+n)}{m}.$$

Summarize it using the formula of $$\tan(\alpha+\beta) = \frac{(\tan\alpha - \tan\beta)}{(1+\tan\alpha \times \tan\beta)}.$$

Then, $$\tan j = \tan\{(s+j)-s\} \qquad \text{Equation (6)}$$
$$= \frac{\tan(s+j)-\tan s}{1+\tan s \times \tan(s+j)}$$
$$= \frac{\frac{n}{m}-\frac{n}{m+R}}{1+\frac{n}{m}\times\frac{n}{m+R}}$$
$$= \frac{\frac{n(m+R)-m\times n}{m(m+R)}}{\frac{m(m+R)+n^2}{m(m+R)}}$$
$$= \frac{mn+nR-mn}{m(m+R)+n^2}.$$

$$\tan j = \frac{nR}{m^2+mR+n^2}$$

$$m^2+mR+n^2 = \frac{nR}{\tan j}$$

$$m^2+mR+n^2 - \frac{nR}{\tan j} = 0 \rightarrow$$

$$\tan i = \tan((s+j+i)-(s+j)) \qquad \text{Equation (7)}$$

$$\tan i = \frac{\frac{L+n}{R+m}-\frac{n}{m}}{1+\frac{L+m}{R+m}\times\frac{n}{m}}$$
$$= \frac{\frac{m(L+n)-n(R+m)}{(R+m)m}}{\frac{(R+m)m+(L+n)n}{(R+m)m}}$$
$$= \frac{mL+mn-nR-mn}{(R+m)m+(L+n)n}$$
$$= \frac{mL-nR}{m^2+mR+nL+n^2}$$

-continued $$m^2 + mR + nL + n^2 = \frac{mL - nR}{\tan i}$$

$$m^2 + mR + nL + n^2 - \frac{mL - nR}{\tan i} = 0 \rightarrow$$

$$\tan h = \tan\{(s + j + i + h) - (s + j + i)\} \quad \text{Equation (8)}$$

$$= \frac{\frac{L+n}{m} - \frac{L+n}{R+m}}{1 + \frac{L+n}{m} \times \frac{L+n}{R+m}}$$

$$= \frac{\frac{(L+n)(R+m) - m(L+n)}{m(R+m)}}{\frac{m(R+m) + (L+n)^2}{m(R+m)}}$$

$$= \frac{(L+n)(R+m) - m(L+n)}{m(R+m) + (L+n)^2}$$

$$= \frac{LR + mL + nR + mn - L - mn}{m^2 + mR + L^2 + 2nL + n^2}$$

$$\tan h = \frac{LR + nR}{m^2 + mR + L^2 + 2nL + n^2}$$

$$m^2 + mR + L^2 + 2nL + n^2 = \frac{LR + nR}{\tan h}$$

$$m^2 + mR + L^2 + 2nL + n^2 - \frac{LR + nR}{\tan h} = 0 \rightarrow$$

$$\tan(j + i) = \tan\{(s + j + i) - s\} = \quad \text{Equation (9)}$$

$$\frac{\frac{L+n}{R+m} - \frac{n}{R+m}}{1 + \frac{L+n}{R+m} \times \frac{n}{R+m}} = \frac{\frac{(R+m)L}{(R+m)^2}}{\frac{(R+m)^2 + nL + n^2}{(R+m)^2}}$$

$$\tan(j + i) = \frac{RL + mL}{R^2 + 2mR + m^2 + nL + n^2}$$

$$R^2 + 2 + m^2 + nL + n^2 = \frac{RL + Lm}{\tan(j+i)}$$

$$R^2 + 2 + m^2 + nL + n^2 - \frac{RL + Lm}{\tan(j+i)} = 0 \rightarrow$$

$$\tan(j + i + h) = \tan\{(s + j + i + h) - s\} \quad \text{Equation (10)}$$

$$= \frac{\frac{L+n}{m} - \frac{n}{R+m}}{1 + \frac{L+n}{m} \times \frac{n}{R+m}}$$

$$= \frac{\frac{(R+m)(L+n) - mn}{m(R+m)}}{\frac{m(R+m) + nL + n^2}{m(R+m)}}$$

$$= \frac{RL + nR + mL + mn - mn}{m(R+m) + nL + n^2}$$

$$\tan(j + i + h) = \frac{RL + nR + mL}{m^2 + mR + nL + n^2}$$

$$m^2 + mR + nL + n^2 = \frac{RL + nR + mL}{\tan(j+i+h)}$$

$$m^2 + mR + nL + n^2 - \frac{RL + nR + mL}{\tan(j+i+h)} = 0 \rightarrow$$

$$\tan(i + h) = \tan\{(s + j + i + h) - (s + j)\} \quad \text{Equation (11)}$$

$$= \frac{\frac{L+n}{m} - \frac{n}{m}}{1 + \frac{L+n}{m} \times \frac{n}{m}}$$

$$= \frac{\frac{mL + mn - mn}{m^2}}{\frac{m^2 + nL + n^2}{m^2}}$$

$$\tan(i + h) = \frac{mL}{m^2 + nL + n^2}$$

$$m^2 + nL + n^2 = \frac{mL}{\tan(i+h)}$$

$$m^2 + nL + n^2 - \frac{mL}{\tan(i+h)} = 0 \rightarrow$$

Here, equation (6)-equation (7) is given by:

$$m^2 + mR + n^2 - \frac{nR}{\tan j} - \quad \text{Equation (12)}$$

$$\left(m^2 + mR + nL + n^2 - \frac{mL - nR}{\tan i}\right) = 0$$

$$-\left(nL + \frac{nR}{\tan j}\right) + \frac{mL - nR}{\tan i} = 0$$

$$\frac{mL}{\tan i} - \left(L + \frac{R}{\tan j} + \frac{R}{\tan i}\right)n = 0$$

$$\frac{L}{\tan i}m = \left(L + \frac{R}{\tan j} + \frac{R}{\tan i}\right)n$$

$$m = \left(L + \frac{R}{\tan j} + \frac{R}{\tan i}\right)n \times \frac{\tan i}{L}n \rightarrow$$

Here, equation (8)-equation (10) is given by:

$$m^2 + mR + L^2 + 2nL + n^2 - \frac{R(L+n)}{\tan h} -$$

$$\left\{m^2 + mR + nL + n^2 - \frac{RL + nR + mL}{\tan(j+i+h)}\right\} = 0$$

$$nL + L^2 - \frac{R(L+n)}{\tan h} + \frac{RL + nR + mL}{\tan(j+i+h)} = 0$$

$$nL + L^2 - \frac{RL}{\tan h} - \frac{nR}{\tan h} +$$

$$\frac{RL}{\tan(j+i+j)} + \frac{nR}{\tan(j+i+h)} + \frac{mL}{\tan(j+i+h)} = 0$$

$$\left(L - \frac{R}{\tan h} + \frac{R}{\tan(j+i+h)}\right)n + \frac{mL}{\tan(j+i+h)} +$$

$$L^2 + RL\left(\frac{1}{\tan(j+i+h)} - \frac{1}{\tan h}\right) = 0$$

Put equation (12) in this. Then, $$\left(L - \frac{R}{\tan h} + \frac{R}{\tan(j+i+h)}\right)n +$$

$$\frac{L \times \left(L + \frac{R}{\tan j} + \frac{R}{\tan i}\right) \times \frac{\tan i}{L} \times n}{\tan(j+i+h)} + L^2 + RL\left(\frac{1}{\tan(j+i+h)} - \frac{1}{\tan h}\right) = 0$$

$$\left(L - \frac{R}{\tan h} + \frac{R}{\tan(j+i+h)}\right)n + \frac{\left(L + \frac{R}{\tan j} + \frac{R}{\tan i}\right) \times \tan i \times n}{\tan(j+i+h)} +$$

$$L^2 + RL\left(\frac{1}{\tan(j+i+h)} - \frac{1}{\tan h}\right)$$

$$n \times \left\{L - \frac{R}{\tan h} + \frac{R}{\tan(j+i+h)} + \frac{L\tan j \tan i + R(\tan i + \tan j)}{\tan j \tan(j+i+h)}\right\} +$$

$$L^2 + RL\left\{\frac{\tan h - \tan(j+i+h)}{\tan(j+i+h)\tan h}\right\}$$

$$n\left\{L - \frac{R}{\tan h} + \frac{R}{\tan(j+i+h)} + \frac{L\tan j \tan i + R(\tan i + \tan j)}{\tan j \tan(j+i+h)}\right\} +$$

$$\frac{\tan h - \tan(j+i+h)}{\tan h \times \tan(j+i+h)}RL + L^2 = 0$$

-continued $$n\frac{L\tan h\tan j\{\tan(j+i+h)+\tan i\}-R\{\tan(j+i+h)\tan j-2\tan h\tan j-\tan h\tan i\}}{\tan h\tan j\tan(j+i+h)}=$$

$$-\frac{RL\{\tan h-\tan(j+i+h)\}+L^2\tan h\tan(j+i+h)}{\tan h\tan(j+i+h)}$$

$$n=-\frac{\tan j\,[RL\times\{\tan h-\tan(j+i+h)\}+L^2\tan h\tan(j+i+h)]}{L\tan h\tan j\times\{\tan(j+i+h)+\tan i\}-R\times\{\tan(j+i+h)\tan j-2\tan h\tan i-\tan h\tan j\}}$$

Meanwhile, from equation (12), $$m=\left(L+\frac{R}{\tan j}+\frac{R}{\tan i}\right)\times\frac{\tan i}{L}n,$$

thus, $$m=\left(L+\frac{R}{\tan i}+\frac{R}{\tan i}\right)\times\frac{\tan i}{L}\times n=\left(L+\frac{R}{\tan i}+\frac{R}{\tan i}\right)\times\frac{\tan i}{L}\times$$

$$\frac{-\tan j[RL\times\{\tan h-\tan(j+i+h)\}-L^2\tan h\tan(j+i+h)]}{L\tan h\tan i\times\{\tan(i+j+h)+\tan i\}-R\times\{\tan(i+j+h)\tan i-2\tan h\tan i-\tan h\tan i\}}$$

$$m=\left(L+\frac{R}{\tan j}+\frac{R}{\tan i}\right)\times\frac{\tan i}{L}\times$$

$$\frac{-\tan j[RL\times\{\tan h-\tan(j+i+h)\}-L^2\tan h\tan(j+i+h)]}{L\tan h\tan j\times\{\tan(j+i+h)+\tan i\}-R\times\{\tan(j+i+h)\tan j-2\tan h\tan i-\tan h\tan j\}}$$

$$m=\left(\frac{L\tan j\tan i+R\tan i+R\tan j}{\tan j\tan i}\right)\times\frac{\tan i}{L}\times$$

$$\frac{-\tan j[RL\times\{\tan h-\tan(j+i+h)\}+L^2\tan h\tan(j+i+h)]}{L\tan h\tan j\times\{\tan(j+i+h)+\tan i\}-R\times\{\tan(j+i+h)\tan j-2\tan h\tan i-\tan h\tan j\}}$$

$$m=\left(\frac{L\tan j\tan i+R\tan i+R\tan j}{\tan j\times L}\right)\times$$

$$\frac{-\tan j[RL\times\{\tan h-\tan(j+i+h)\}+L^2\tan h\tan(j+i+h)]}{L\tan h\tan j\times\{\tan(j+i+h)+\tan i\}-R\times\{\tan(j+i+h)\tan j-2\tan h\tan i-\tan h\tan j\}}$$

$$m=-\frac{(L\tan j\tan i+R\tan i+R\tan j)\left[\begin{array}{c}RL\times\{\tan h-\tan(j+i+h)\}+\\ L^2\tan h\tan(j+i+h)\end{array}\right]}{L^2\tan h\tan j\times\{\tan(j+i+h)+\tan i\}-LR\times\{\tan(j+i+h)\tan j-2\tan h\tan i-\tan h\tan j\}}$$

That is, m and n may be expressed by using known constants L (distance between rings) and R (diameter of ring), and tan h, tan i, tan j, tan (j+i+h).

Meanwhile, ∠GPH=h, ∠HPI=i, and ∠IPJ=j may be obtained from the lengths of respective sides of triangles ΔGPH, ΔHPI, and ΔHPJ.

Summarize using the second raw of cosines:

$$\cos A=\frac{b^2+c^2-a^2}{2bc}.$$

Then, $$\cos h=\frac{(\overline{PG})^2+(\overline{PH})^2-(\overline{GH})^2}{2\overline{PG}\times\overline{PH}}$$

$$\cos i=\frac{(\overline{PH})^2+(\overline{PI})^2-(\overline{HI})^2}{2\overline{PH}\times\overline{PI}}$$

$$\cos j=\frac{(\overline{PI})^2+(\overline{PJ})^2-(\overline{IJ})^2}{2\overline{PI}\times\overline{PJ}}.$$

Meanwhile, since the coordinates of points P, G, H, I, and J are known, the distance of each straight line may be obtained using the formula between two points.

Through these, h, i, and j values are obtained and tangent values thereof may be obtained.

Through these, m and n may be obtained.

As described above, three-dimensional spatial coordinates of points G', H', I', and J' may be obtained, and points $O_a$ and $O_b$ which bisect line segments $\overline{G'H'}$ and $\overline{I'J'}$ are calculated to obtain the second reality three-dimensional spatial coordinates of the image of the medical device.

In addition, three-dimensional spatial coordinates of the points on the ring, which are indicated by markers, may be calculated using three-dimensional spatial coordinates of points G', H', I', J', $O_a$, and $O_b$.

Figure 11:
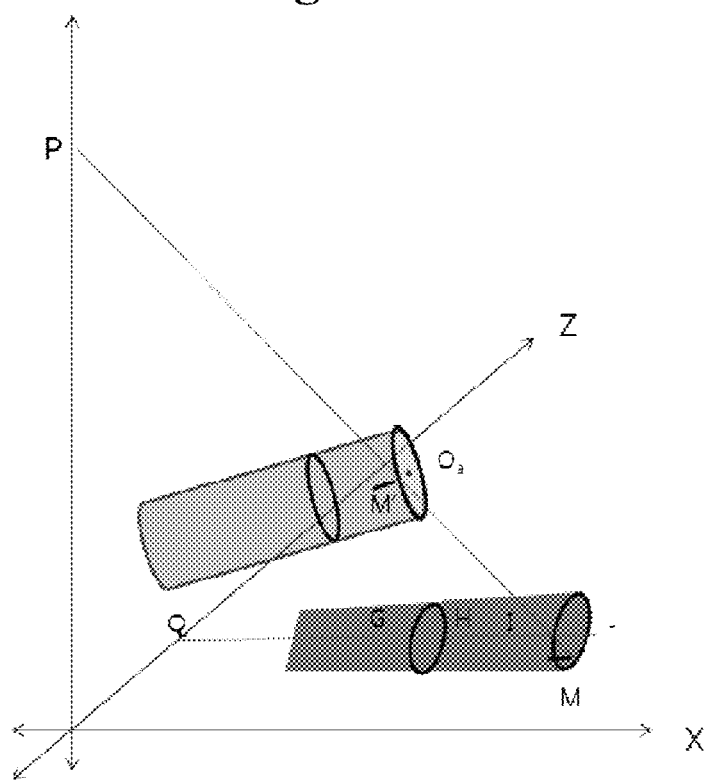
FIG. 11 shows a medical device including a marker indicating one point of a ring, an X-ray light source P, and an image of the medical device on a detector. The origin point of the ring is represented by $O_a$; the intersection point of the ring and the marker is represented by M'; and the image thereof is represented by M. Points G, H, I, and J of FIG. 10 are shown.

FIG. 11 shows the medical device including a marker indicating one point on the ring, the X-ray light source P, and an image of the medical device on the detector, and here, the center point of the ring is designated as Oa, the intersection point of the ring and the marker is designated as M', and the image thereof is designated as M. Points G, H, I, and J of FIG. 10 are shown.

Point M' is on straight line $\overline{PM}$ passing through points P and M, and distanced from the center point $O_a$ of the circle by R/2 since point M' is on the ring.

Assume that P ($p_1$, $p_2$, $p_3$) and M ($m_1$, $m_2$, $m_3$) and $O_a$ ($a_1$, $a_2$, $a_3$) and $O_b$ ($b_1$, $b_2$, $b_3$). Then, the equation of $\overline{PM}$ is given by $$\frac{x-p_1}{m_1-p_1}=\frac{y-p_2}{m_2-p_2}=\frac{z-p_3}{m_3-p_3}.$$

Assume that $m_1-p_1=\alpha$, $m_2-p_2=\beta$, and $m_3-p_3=\gamma$, and coordinates of M' are ($m'_1$, $m'_2$, $m'_3$). Then, $$\frac{m'_1-p_1}{\alpha}=\frac{m'_2-p_2}{\beta}=\frac{m'_3-p_3}{\gamma}\rightarrow \qquad \text{Equation (13)}$$

The distance between M' and $O_a$ is R/2, and thus, $$(b_1-m'_1)^2+(b_2-m'_2)^2+(b_3-m'_3)^2=\frac{R^2}{4}\rightarrow \qquad \text{Equation (14)}$$

In addition, since point M' is one point on the circle which has point $O_a$ as the center point and passes through points A', B', G', and H', point M' and the circle are present on the same plane. The line connecting points $O_a$ and $O_b$ is a normal line to this plane.

The equation of this plane is given by $$\frac{x - a_1}{a_1 - b_1} + \frac{y - a_2}{a_2 - b_2} + \frac{z - a_3}{a_3 - b_3} = 0$$

Therefore, $$\frac{m'_1 - a_1}{a_1 - b_1} + \frac{m'_2 - a_2}{a_2 - b_2} + \frac{m'_3 - a_3}{a_3 - b_3} = 0 \rightarrow \quad \text{Equation (15)}$$

By summarizing equations (13), (14), and (15),

M' (m'$_1$, m'$_2$, m'$_3$) can be obtained.

∠M'O$_a$G' and ∠M'O$_a$H' can be obtained from the obtained coordinates of M', G', O$_a$, and H', and are used to find a relative position of the marker, thereby easily operating the medical device.

In cases where the rings are parallel with each other without a flexure, the position of the medical device between the rings can be found, and thus a three-dimensional image can be implemented.

In addition, in cases where a marker capable of indicating a specific site on the ring is used, the relative position of an internal portion of the medical device can be found.

At least one marker may be attached on the ring as needed. In cases where the medical device may have a flexure portion, two rings as above are attached before and after the flexure portion, thereby obtaining a three-dimensional flexible image. The number of flexure portions may be two or more.

In cases where one light source instead of a plurality of light sources is used in X-ray fluoroscopy, a predetermined marker is needed on the medical device. In addition, even in cases where a plurality of light sources are used, the use of a predetermined marker may be a supplement help in calculating the reality three-dimensional spatial coordinates of the medical device.

The predetermined marker is an identifier capable of recognizing the rotation, direction, and the like, of the medical device. In cases where a plurality of light sources are used as described above, the rotation, direction, and the like, of the medical device can be recognized. However, in cases where the three-dimensional spatial coordinates of the medical device are obtained by using one light source, it is difficult to find information about accurate rotation or direction of the medical device.

In cases where one light source is used, X-rays are irradiated to the medical device using an X-ray light source, and then an X-ray fluoroscopy image of the medical device through the X-ray light source is detected by an X-ray detector. After that, the three-dimensional spatial coordinates of the medical device are obtained based on the image of the medical device, which is detected by the X-ray detector.

The medical device of the present invention may include a radio wave reflector.

In this case, a first microwave generator generates a microwave toward the radio wave reflector.

Here, the microwave needs to have a frequency band which is harmless to humans or various medical devices in a surgical field.

In addition, a second microwave generator generates a microwave toward the radio wave reflector. The microwave by the second microwave generator and the microwave by the first microwave generator have different frequency bands, and should not cause mutual interference. Preferably, the microwave by the second microwave generator and the microwave by the first microwave generator are mutually orthogonal to each other.

After that, a microwave receiver receives a first microwave and a second microwave, which are reflected through the radio wave reflector, separates a radio wave by the first microwave and a radio wave by the second microwave through filtering, and measuring the time during which the microwaves are transmitted, reflected, and received, thereby calculating the position of the radio wave reflector, that is, the position of the medical device.

Step (c): Determining Third Reality Three-Dimensional Spatial Coordinates of Periphery of Medical Device A three-dimensional image of the periphery of the medical device is obtained from the imaging unit of the medical device, and third reality three-dimensional spatial coordinates thereof are determined.

According to an embodiment of the present invention, the third reality three-dimensional spatial coordinates are on an orthogonal coordinate system.

The three-dimensional image of the periphery of the medical device may be obtained using a plurality of (e.g., two) cameras.

According to an embodiment of the present invention, the camera as the imaging unit includes two rings and markers attached on one-sided portions of the respective rings, as an identification part. The rings may be positioned on the same plane or a different plane with respect to an image sensor of the camera. Even though the rings are positioned on a different plane from the image sensor, the three-dimensional position of the image sensor can be obtained as long as the image sensor is positioned on the plane parallel with a plane including the rings and the distance between the two planes is known. The markers may be attached to the rings so as to coincide with the directions of the x-axis and the y-axis of the image sensor.

As described above, when the identification part is attached to the imaging unit of the medical device, the reality three-dimensional coordinates of the three-dimensional image obtained by the imaging unit can be calculated by using the identification part. In addition, the imaging unit may be positioned in vivo or ex vivo.

First, a three-dimensional endoscope using a 3D camera is exemplified. The 3D camera is composed of two cameras. When a pair of rings and markers indicating points on the rings are displayed on each of the cameras in directions of x-axis and y-axis of the image sensor, the center axis of the lens of each of the cameras and x- and y-axial vectors of the image sensor can be calculated by X-ray fluoroscopy, and based on these, the reality three-dimensional spatial coordinates of the three-dimensional image of the 3D camera can be calculated.

Figure 13:
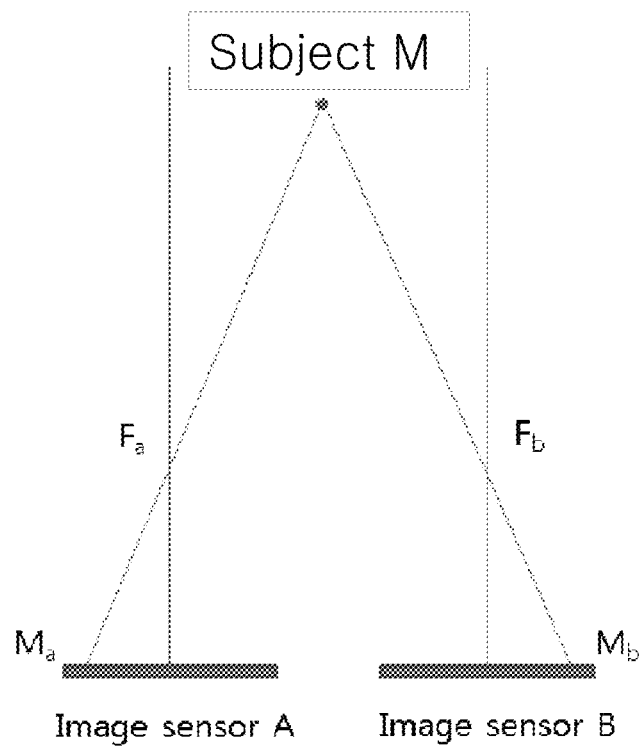
FIG. 13 is a view showing images of a subject focused on 3D cameras.

More specifically, the respective cameras are designated as camera A (image sensor A of FIG. 13) and camera B (image sensor B of FIG. 13). Assume that the straight line constituting the center axis of the lens of camera A is represented by $Z_a$, the straight line constituting the horizontal axis on the plane of the image sensor of camera A is represented by $X_a$, the straight line constituting the vertical axis is represented by $Y_a$, and the intersection point of $X_a$ and $Y_a$ is represented by $O_a$. Then, straight line $Z_a$, is perpendicular to $X_a$ and $Z_a$ while passing through $O_a$. Assume that, when the image of subject M is captured, the image (point) of the subject captured by camera A is represented by $M_a'$, the one-to-one match point on the image sensor is represented by $M_a$ and the focal point of camera A is represented by $F_a$. Then, M is the point on the line passing through $F_a$ and $M_a$.

The center axis of the lens of the camera, as described above, can be calculated from radiation images of a pair of rings installed on an external surface of the cylinder-shaped camera, and the vectors of $X_a$ and $Y_a$ can be calculated using the markers indicating points on the rings. Furthermore, the coordinates of the center point of the image sensor, that is, $O_a$, can be calculated. When the vectors of $X_a$ and $Y_a$ are known and the reality three-dimensional spatial coordinates of $O_a$ are known, the reality three-dimensional spatial coordinates of $M_a$ can be calculated by the method illustrated in FIG. 1. In addition, the reality three-dimensional spatial coordinates of $F_a$ are positioned on the center axis of the lens, and can be mechanically obtained. The equation of straight line $\overline{M_aF_a}$ can be calculated by using the reality three-dimensional spatial coordinates of points $F_a$ and $M_a$. Since point M is positioned on the extension line of the straight line, the equation of straight line $\overline{M_aF_a}$ is identical to the equation of straight line $\overline{M_aM}$.

Since coordinates of $O_b$, $M_b$, and $F_b$ of camera B can be found in the same manner, the equation of the straight line passing through points M and $M_b$ can be obtained. In addition, since point M is the intersection point of the straight line passing through points M and $M_a$ and the straight line passing through points M and $M_b$, the coordinates of point M can be obtained.

Therefore, the image of the 3D camera can be made into reality three-dimensional spatial coordinates, which are then linked with the reality three-dimensional spatial coordinates of the different three-dimensional image, which has been previously obtained by X-ray fluoroscopy, thereby realizing a visual image.

Figure 12:
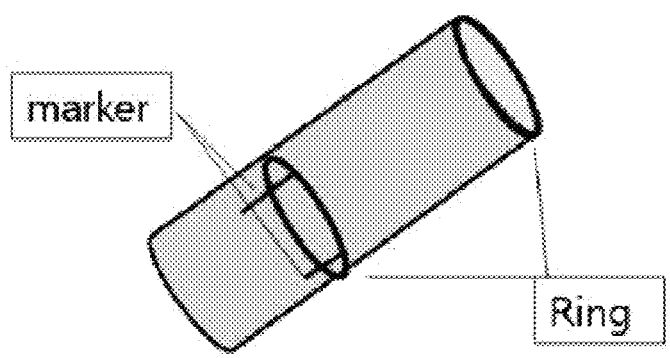
FIG. 12 is a perspective view of an external shape of a camera attached with a pair of rings and bar-shaped markers indicating a particular site of the ring.

As shown in FIG. 12, straight line connecting the centers of two rings is allowed to coincide with the center axis of the lens, and while specific sites of the ring, indicated by the markers, are on the same plane as the image sensor (camera A or B), the points are connected to the center point of the image sensor, thereby showing vectors of the x-axis and the y-axis of the image sensor. In addition, the markers corresponding to the x-axis and the y-axis are differently displayed for differentiation. For example, one maker is displayed longer and the other marker is displayed shorter.

Through the method described above, the center axis of the two rings is calculated and three-dimensional coordinates of the marker are calculated, thereby finding the vectors of the x axis and y axis of the image sensor and the center axis (z axis) of the lens and the center point of the image sensor.

Referring to FIG. 13, if the focal point of camera A is $F_a$ at the shooting, the image $M_a$ of subject M is the intersection point of the straight line passing through M and $F_a$ and the image sensor.

Therefore, M is on the straight line passing through $F_a$ and $M_a$. For the same reason, M is on the straight line passing through $F_b$ and $M_b$.

Figure 14:
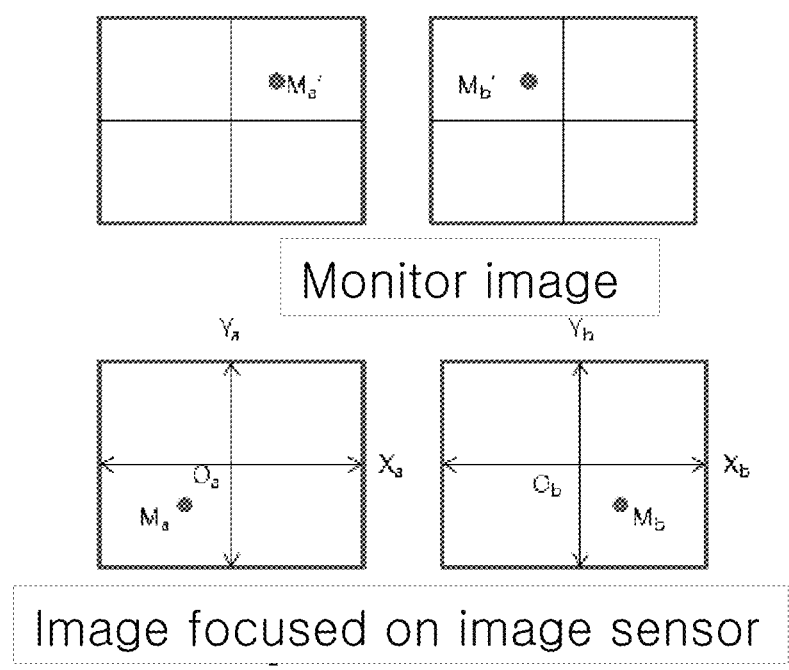
FIG. 14 is a view showing monitor images of a subject and images of the subject focused on image sensors.
Figure 15:
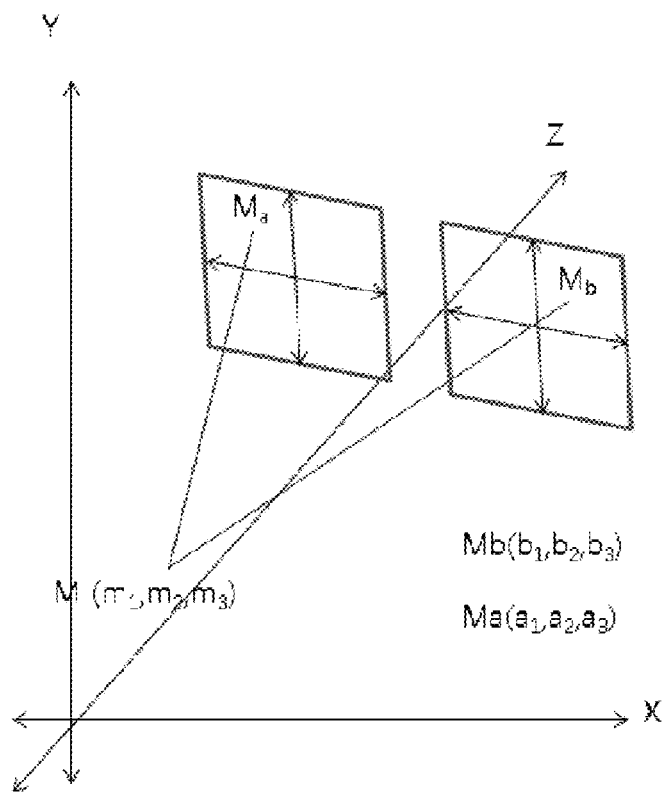
FIG. 15 is a view showing schematic straight lines of the image in FIG. 12 using three-dimensional coordinates.

In FIG. 14, three-dimensional coordinates of the center points of the image sensors, $O_a$ and $O_b$, can be calculated from radiation images of two pairs of rings installed on external surfaces of the respective cameras (described in FIG. 10).

In addition, the markers on the ring are displayed on the x-axis and the y-axis of the image sensor, and the coordinates of the specific sites on the ring, indicated by the markers, can be calculated by the radiation images, and thus the three-dimensional vectors of the x-axis and the y-axis of the image of each camera (described in FIG. 11).

In addition, the focal point of each camera is on the line which is perpendicular to the x-axis and the y-axis of the image sensor and passes through the center point $O_a$ or $O_b$ of the image sensor, that is, the line passing through the center points of one pair of rings, and the focal distance is determined by controlling the lens, and thus the three-dimensional coordinates of focal point $F_a$ or $F_b$ of each camera can be obtained.

Meanwhile, subject M is the intersection point of the straight line passing through $M_a$ and $F_a$ and the straight line passing through $M_b$ and $F_b$, and the three-dimensional coordinates of points $M_a$, $F_b$, $M_b$, and $F_b$ are known, and thus the point at which the two lines intersect in the three-dimensional space can be obtained.

More specifically, as shown in FIG. 14,

Assume that M $(m_1, m_2, m_3)$, $M_a$ $(a_1, a_2, a_3)$, $M_b$ $(b_1, b_2, b_3)$, $F_a$ $(c_1, c_2, c_3)$, and $F_b$ $(d_1, d_2, d_3)$, $a_1 - c_1 = \alpha_1$, $a_2 - c_2 = \alpha_2$, $a_3 - c_3 = \alpha_3$, and
$b_1 - d_1 = \beta_1$, $b_2 - d_2 = \beta_2$, $b_3 - d_3 = \beta_3$ Then, straight line $\overline{MM_a}$ is $$\frac{x - a_1}{\alpha_1} = \frac{y - a_2}{\alpha_2} = \frac{z - a_3}{\alpha_3},$$

and
straight line $\overline{MM_b}$ is $$\frac{x - b_1}{\beta_1} = \frac{y - b_2}{\beta_2} = \frac{z - b_3}{\beta_3}.$$

Since M $(m_1, m_2, m_3)$ is the intersection point of the two straight lines, $$\frac{m_1 - a_1}{\alpha_1} = \frac{m_2 - a_2}{\alpha_2} = \frac{m_3 - a_3}{\alpha_3}$$

$$m_2 = \frac{\alpha_2}{\alpha_1} \times (m_1 - a_1) + a_2$$

$$\frac{m_1 - b_1}{\beta_1} = \frac{m_2 - b_2}{\beta_2} = \frac{m_3 - b_3}{\beta_3}$$

$$m_2 = \frac{\beta_2}{\beta_1} \times (m_1 - b_1) + b_2$$

$$\frac{\alpha_2}{\alpha_1} \times (m_1 - a_1) + a_2 = \frac{\beta_2}{\beta_1} \times (m_1 - b_1) + b_2$$

$$\left(\frac{\alpha_2}{\alpha_1} - \frac{\beta_2}{\beta_1}\right) m_1 = \frac{\alpha_2}{\alpha_1} a_1 - \frac{\beta_2}{\beta_1} b_1 - a_2 + b_2$$

$$m_1 = \frac{\frac{\alpha_2}{\alpha_1} a_1 - \frac{\beta_2}{\beta_1} b_1 - a_2 + b_2}{\frac{\alpha_2}{\alpha_1} - \frac{\beta_2}{\beta_1}}$$

$$m_1 = \frac{\frac{\alpha_2 \beta_1 a_1 + \alpha_1 \beta_2 b_1 - \alpha_1 \beta_1 a_2 + \alpha_1 \beta_1 b_2}{\alpha_1 \beta_1}}{\frac{\alpha_2 \beta_1 + \alpha_1 \beta_2}{\alpha_1 \beta_1}}$$

$$m_1 = \frac{\alpha_2 \beta_1 a_1 + \alpha_1 \beta_2 b_2 - \alpha_1 \beta_1 a_2 + \alpha_1 \beta_1 b_2}{\alpha_2 \beta_1 + \alpha_1 \beta_2}$$

Here, $m_2$ and $m_3$ can be obtained by putting these values in the equation of straight line.

That is, the reality three-dimensional coordinates of the three-dimensional image, M ($m_1$, $m_2$, $m_3$) of the 3D camera can be obtained, and thus the three-dimensional image on the three-dimensional coordinates can be implemented.

Take an ultrasonography equipment as an example of the imaging unit. When an ultrasonic probe is radiographed, if the position of the scan line of the radiographed ultrasonic probe is made into three-dimensional spatial coordinates, the three-dimensional spatial coordinates of this image can be made into reality three-dimensional spatial coordinates since the ultrasonography image is based on the scan line.

Figure 16:
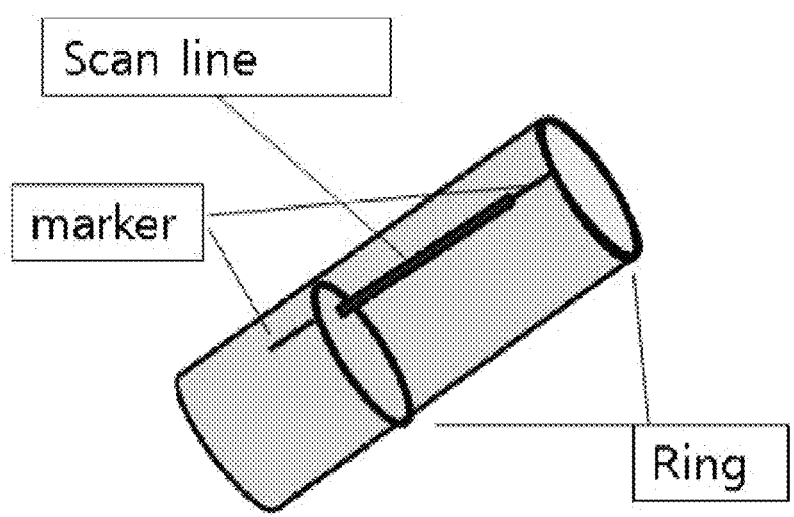
FIG. 16 is a schematic view showing an ultrasonography imaging medical device with an identification including rings, markers, and a scan line.

Referring to FIG. 16, rings, which have the same center axis and are parallel with each other, are mounted on both ends of the ultrasonic probe, and markers displaying a scan line are formed on outer edges of the rings, so that the reality three-dimensional spatial coordinates of the scan line can be obtained by the method as described above. The ultrasonography image expresses a relative position from the scan line, and thus, based on this, the three-dimensional coordinates of the ultrasonography image can be made into reality three-dimensional spatial coordinates. If the ultrasonography image has three dimensions, the ultrasonography image can be three-dimensionally expressed, and if the ultrasonography image has two dimensions, the ultrasonography image can be two-dimensionally expressed in the three-dimensional image. This image may be implemented in combination with another three-dimensional image.

Step (d): Examining Images on Same Coordinates in Three Three-Dimensional Spatial Coordinates As described above, the first reality three-dimensional spatial coordinates of the three-dimensional image of the human body, the second reality three-dimensional spatial coordinates of the image of the medical device, and the third reality three-dimensional spatial coordinates of the three-dimensional image of the periphery of the medical device are determined, and then images on the same coordinates in the three three-dimensional spatial coordinates are examined.

Step (e): Producing Complex Reality Three-Dimensional Image

If one image is on the same coordinates in the three three-dimensional spatial coordinates, the image is selected, and if a plurality of images are on the same coordinates, necessary images among the plurality of images are selected to produce a complex reality three-dimensional image. Thus, an accurate procedure can be performed in real time using an effect of a kind of augmented reality.

According to an embodiment of the present invention, the method of the present invention further includes a step of determining a three-dimensional image of a periodic-mobility human body part (e.g., heart), which has periodic mobility and generates signals (e.g., electrocardiogram, blood pressure, organ pressure, and abdominal pressure) linked with the periodic mobility, and fourth reality spatial coordinates thereof. Step (d) is performed by using the first reality three-dimensional spatial coordinates, the second reality three-dimensional spatial coordinates, the third reality three-dimensional spatial coordinates, and the fourth reality spatial coordinates. For example, the surface and the internal structure of the heart are uniformly changed according to the period of the heart. In addition, the change is uniform according to the position of the waveform of the electrocardiogram. Therefore, the morphological structure of the heart is uniform according to the position of the waveform of the electrocardiogram. Thus, the three-dimensional image of the heart according to the position of the waveform of the electrocardiogram is obtained (using, for example, esophagus and heart ultrasonic waves), and the three-dimensional coordinates of the image are calculated when a patient is placed on the operation table, and as a result, the real-time three-dimensional image of the heart can be implemented in linkage with the electrocardiogram even without obtaining the three-dimensional image of the heart in real time. According to another embodiment, a complex image of the heart is configured by obtaining a three-dimensional image of CT or MRI scans according to the electrocardiogram outside the operating place, obtaining a two- or three-dimensional image of heart ultrasonic waves according to the electrocardiogram, and matching these images using the same region based on the coordinates. Here, there are several complex images of the heart depending on the period of the electrocardiogram. After that, the reality three-dimensional spatial coordinates of the heart using esophageal echocardiography are allowed to coincide with the three-dimensional spatial coordinates of the complex image of the heart on the operation table, to obtain fourth real spatial coordinates of the complex image of the heart, thereby finding fourth real spatial coordinates of the complex image of the heart according to the period of the electrocardiogram. The complex reality three-dimensional image may be implemented using the esophageal ultrasonography image and the period of the electrocardiogram, or separately using the esophageal ultrasonography image and the period of the electrocardiogram.

System for Producing Complex Reality Three-Dimensional Image

A system of the present invention includes a first processor for calculating (i) first reality three-dimensional spatial coordinates of a three-dimensional image of the human body obtained before a medical device is applied to a subject; (ii) second reality three-dimensional spatial coordinates of an image of the medical device applied to the subject; and (iii) third reality three-dimensional spatial coordinates of a three-dimensional image of the periphery of the medical device, by using the same coordinate system. Further, the system of the present invention includes a second processor for examining images on the same coordinates in the three three-dimensional spatial coordinates, by using the first reality three-dimensional spatial coordinates, the second reality three-dimensional spatial, and the third reality three-dimensional spatial, and then, if one image is on the same coordinates, selecting the one image, and if a plurality of images are on the same coordinates, necessary image(s) are selected from the plurality of images, thereby producing a complex reality three-dimensional image.

The system of the present invention is divided into the first processor and the second processor as elements, for definitely describing the present invention, but substantially, the two processors may be manufactured as one processor. Therefore, it would be obvious to a person skilled in the art that a processor capable of performing all of the above processes is also included in the scope of the present invention.

The system of the present invention may further include a computer-readable storage medium coupled with the processors. The storage medium is not particularly limited, and thus includes various storage media known in the art, for example, CD-R, CD-ROM, DVD, data signal embedded in a carrier wave, flash memory, floppy disk, hard drive, magnetic tape, MINIDISC, nonvolatile memory card, EEPROM, optical disk, optical storage medium, RAM, ROM, system memory, and a Web server, but is not limited thereto.

The system of the present invention may be constructed in various manners. For example, the system of the present invention may be constructed of a multi-processor computer array, a Web server, a multi-user/interactive system, or the like.

The system of the present invention may include various elements, and for example, the system of the present invention may constructed to include a data base storing information about images and spatial coordinates, a processor calculating reality three-dimensional spatial coordinates using the same coordinate system, and a processor selecting necessary image(s) to produce a complex reality three-dimensional image.

The invention claimed is:

1. A method for producing a complex reality three-dimensional image, the method comprising:
   (a) determining first reality three-dimensional spatial coordinates of a three-dimensional image of the human body of a subject or a particular part thereof before a medical device is applied to the a subject,
   (b) determining second reality three-dimensional spatial coordinates of an image of the medical device to be applied within the body of the subject, the medical device including an imaging unit and an at least one identification part for recognizing the position of the medical device,
   wherein the at least one identification part includes one or more ring-shaped identification parts, one or more sphere-shaped identification parts, and/or one or more markers,
   wherein if the sum of ring-shaped identification parts, sphere-shaped identification parts, and the markers is two or more, each identification part is mounted on the medical device at different positions or has different imaging characteristics;
   wherein the first and second reality three-dimensional spatial coordinates is determined using electromagnetic radiation;
   (c) obtaining a three-dimensional image of the periphery of the medical device when placed within the body of the subject from the imaging unit of the medical device, and determining third reality three-dimensional spatial coordinates of the obtained image, the first reality three-dimensional spatial coordinates, the second reality three-dimensional spatial coordinates, and the third reality three-dimensional spatial coordinates being determined by using the same coordinate system;
   (d) examining images on the same coordinates in the three-dimensional spatial coordinates as determined in steps (a), (b), and (c); and
   (e) producing a complex reality three-dimensional image by selecting, if one image is on the same coordinates, the one image, and selecting, if multiple images are on the same coordinates, necessary image(s) from the multiple images;
   wherein the medical device includes a radio wave reflector and step (b) comprises the following sub-steps of:
   (b-1) generating a first microwave toward the radio wave reflector using a first microwave generator;
   (b-2) generating a second microwave toward the radio wave reflector using a second microwave generator;
   (b-3), after sub-steps (b-1) and (b-2), receiving the first and second microwaves reflected from the radio wave reflector; and
   (b-4) determining the second reality three-dimensional spatial coordinates of the image of the medical device by using information of the received first and second microwaves.

2. The method of claim 1, wherein the same coordinate system used to determine the first reality three-dimensional spatial coordinates, the second reality three-dimensional spatial coordinates, and the third reality three-dimensional spatial coordinates is set based on an operation table on which the medical device is applied to the subject.

3. The method of claim 1, wherein the three-dimensional image of the human body used in step (a) is an X-ray fluoroscopy image, a computed tomography (CT) image, a magnetic resonance imaging (MRI) image, a positron emission tomography (PET) image, a PET/CT image, a PET/MRI image, a radioisotope imaging (RI) image, an ultrasonography image, or a complex image thereof.

4. The method of claim 1, wherein the electromagnetic radiation is X-ray radiation or radiofrequency electromagnetic radiation.

5. The method of claim 4, wherein the first reality three-dimensional spatial coordinates and the second reality three-dimensional spatial coordinates are determined using X-ray fluoroscopy.

6. The method of claim 4, wherein the first reality three-dimensional spatial coordinates and the second reality three-dimensional spatial coordinates are determined using mono-plan fluoroscopy, bi-plan fluoroscopy, or multi-plan fluoroscopy.

7. The method of claim 1, wherein step (a) comprises the following sub-steps of:
   (a-1) irradiating X-rays toward the particular part of the human body of the subject using a first X-ray light source;
   (a-2) detecting an X-ray fluoroscopy image of the human body by the first X-ray light source, using a first X-ray detector;
   (a-3) irradiating X-rays toward the particular part of the human body to cross the X-rays by the first X-ray light source, using a second X-ray light source;
   (a-4) detecting an X-ray fluoroscopy image of the human body by the second X-ray light source, using a second X-ray detector; and
   (a-5) determining the first reality three-dimensional spatial coordinates of the three-dimensional image of the human body by using the human body images detected by the first X-ray detector and the second X-ray detector.

8. The method of claim 7, wherein sub-step (a-5) comprises:
   (a-5-1) determining three-dimensional spatial coordinates of the three-dimensional image of the particular part of the human body positioned between the first X-ray light source and the first X-ray detector, by using physical three-dimensional coordinate information of the first X-ray light source and the first X-ray detector, distance information therebetween, and size information of the particular part of the human body detected by the first X-ray detector, and determining three-dimensional spatial coordinates of the three-dimensional image of the particular part of the human body positioned between the second X-ray light source and the second X-ray detector, by using physical three-dimensional coordinate information of the second X-ray light source and the second X-ray detector, distance information therebetween, and size information of the particular portion of the human body detected by the second X-ray detector;

(a-5-2) determining three-dimensional spatial coordinates of the particular part of the human body, by using the three-dimensional spatial coordinates of the three-dimensional image of the particular part of the human body positioned between the first X-ray light source and the first X-ray detector and the three-dimensional spatial coordinates of the three-dimensional image of the particular part of the human body positioned between the second X-ray light source and the second X-ray detector; and (a-5-3) allowing the three-dimensional spatial coordinates of the particular part of the human body to coincide with the three-dimensional spatial coordinates of the three-dimensional image of the human body of step (a) to determine the first reality three-dimensional spatial coordinates of the three-dimensional image of the human body.

9. The method of claim 1, wherein in cases where the number of markers is two or more, the markers have different imaging characteristics.

10. The method of claim 1, wherein the second reality three-dimensional spatial coordinates are determined using one or two or more X-ray fluoroscopy images, and wherein step (b) comprises the following sub-steps of:

(b-1) irradiating X-rays toward the medical device using an X-ray light source;

(b-2) detecting an X-ray fluoroscopy image of the medical device by the X-ray light source, by using an X-ray detector; and (b-3) determining the second reality three-dimensional spatial coordinates of the image of the medical device, by using the through-position of the identification part, which is seen through on the X-ray fluoroscopy image.

11. The method of claim 10, wherein in sub-step (b-3), the second reality three-dimensional spatial coordinates of the image of the medical device and three-dimensional spatial coordinates of the marker are determined by using the through-position of the identification part, which is seen through on the X-ray fluoroscopy image, thereby grasping the relative position of an internal portion of the medical device from the three-dimensional spatial coordinates of the marker.

12. The method of claim 10, wherein sub-step (b-3) is performed using three-dimensional position information of the identification part, or three-dimensional position information and dimension information of the identification part.

13. The method of claim 1, wherein the imaging unit includes a plurality of cameras, the three-dimensional image of the periphery of the medical device being obtained using the plurality of cameras in step (c).

14. The method of claim 13, wherein the camera as the imaging unit includes an identification part.

15. The method of claim 1, wherein the imaging unit is an ultrasonic probe, the three-dimensional image of the periphery of the medical device being obtained using the ultrasonic probe in step (c).

16. The method of claim 15, wherein the ultrasonic probe as the imaging unit includes an identification part.

17. The method of claim 1, wherein the three-dimensional image of the human body of step (a) and the three-dimensional image of the periphery of the medical device of step (c) are different kinds of images.

18. The method of claim 1, further comprising a step of determining a three-dimensional image of a periodic-mobility human body part, which has periodic mobility and generates signals linked with the periodic mobility, and fourth reality spatial coordinates thereof, wherein step (d) is performed by using the first reality three-dimensional spatial coordinates, the second reality three-dimensional spatial coordinates, the third reality three-dimensional spatial coordinates, and the fourth reality spatial coordinates.

19. A system for producing a complex reality three-dimensional image, the system comprising:

(a) a first processor for calculating (i) first reality three-dimensional spatial coordinates of a three-dimensional image of the human body obtained before a medical device is applied to a subject; (ii) second reality three-dimensional spatial coordinates of an image of the medical device to be applied within the body of the subject; and (iii) third reality three-dimensional spatial coordinates of a three-dimensional image of the periphery of the medical device when placed within the body of the subject, by using the same coordinate system;

wherein the medical device includes an imaging unit and at least one identification part for recognizing the position of the medical device, wherein the at least one identification part includes one or more ring-shaped identification parts, one or more sphere-shaped identification parts, and/or one or more markers, wherein if the sum of ring-shaped identification parts, sphere-shaped identification parts, and the markers is two or more, each part is mounted on the medical device at different positions or has different imaging characteristics, and wherein the first and second reality three-dimensional spatial coordinates is determined using an electromagnetic radiation device;

(b) a second processor for examining images on the same coordinates in the three-dimensional spatial coordinates as determined in parts (a)(i) through (a)(iii), by using the first reality three-dimensional spatial coordinates, the second reality three-dimensional spatial, and the third reality three-dimensional spatial coordinates, and then, selecting, if one image is on the same coordinates, the one image, and selecting, if a plurality of images are on the same coordinates, necessary image(s) from the plurality of images, to produce a complex reality three-dimensional image; and (c) a medical device including an identification part for recognizing the position of the medical device and a radio wave reflector, wherein when the first processor is calculating said second reality three-dimensional spatial coordinates of said image of said medical device when applied within the body of the subject, this process comprises the steps of (1) generating a first microwave toward the radio wave reflector using a first microwave generator; (2) generating a second microwave toward the radio wave reflector using a second microwave generator; (3), after sub-steps (1) and (2), receiving the first and second microwaves reflected from the radio wave reflector; and (4) determining the second reality three-dimensional spatial coordinates of the image of the medical device by using information of the received first and second microwaves.

20. The system of claim 19, wherein the first reality three-dimensional spatial coordinates, the second reality three-dimensional spatial coordinates, and the third reality three-dimensional spatial coordinates are on an orthogonal coordinate system.

21. The system of claim 19, wherein the same coordinate system used to determine the first reality three-dimensional spatial coordinates, the second reality three-dimensional spatial coordinates, and the third reality three-dimensional spatial coordinates is set based on an operation table on which the medical device is applied to the subject.

22. The system of claim 19, further comprising an X-ray fluoroscopy imaging device, a computed tomography (CT) imaging device, a magnetic resonance imaging (MRI) imaging device, a positron emission tomography (PET) imaging device, a PET/CT imaging device, a PET/MRI imaging device, a radioisotope imaging (RI) imaging device, or an ultrasonography imaging device, for obtaining the three-dimensional image of the human body.

23. The system of claim 19, wherein the electromagnetic radiation device is an X-ray fluoroscopy imaging device or a radiofrequency electromagnetic radiation device.

24. The system of claim 19, wherein the first reality three-dimensional spatial coordinates and the second reality three-dimensional spatial coordinates are calculated by using information obtained from mono-plan fluoroscopy, bi-plan fluoroscopy, or multi-plan fluoroscopy.

25. The system of claim 19, wherein the first reality three-dimensional spatial coordinates are determined using three-dimensional spatial coordinates of the three-dimensional image of the human body obtained before the medical device is applied to the subject, and reality three-dimensional spatial coordinates of a particular part of the subject human body.

26. The system of claim 25, wherein the first reality three-dimensional spatial coordinates are calculated using information obtained from mono- or bi-plan fluoroscopy, the information including: (i) physical three-dimensional coordinate information of a first X-ray light source and a first X-ray detector, distance information therebetween, and size information of the particular part of the human body detected by the first X-ray detector; (ii) physical three-dimensional coordinate information of a second X-ray light source and a second X-ray detector, distance information therebetween, and size information of the particular part of the human body detected by the second X-ray detector; and (iii) three-dimensional spatial coordinates of the three-dimensional image of the human body.

27. The system of claim 19, wherein the identification part of the medical device includes at least one of: (i) at least one sphere-shaped identification part, (ii) at least one ring-shaped identification part, (iii) an identification part including a ring and at least one marker indicating a specific site of the ring, (iv) an identification part including at least one pair of rings, (v) an identification part including at least one pair of rings and at least one marker indicating specific sites of the rings, or (vi) an identification part including markers respectively indicating three differentiated points, the three points of (vi) the identification part being differentiated by using markers with different images, indicating the respective points, or indicating the points using ends of linear markers having differentiated images or intersection points of the markers.

28. The system of claim 27, wherein the identification part includes two or more rings and one or more makers, the two or more rings being mounted on the medical device at different positions, the one or more markers being attached to one side of each of the rings.

29. The system of claim 28, wherein the two or more rings have different imaging characteristics.

30. The system of claim 28, wherein in cases where the number of markers is two or more, the markers have different imaging characteristics.

31. The system of claim 27, wherein the second reality three-dimensional spatial coordinates are calculated by using the through-positions of the rings of the identification part, which are seen through on an X-ray fluoroscopy image.

32. The system of claim 31, wherein the second reality three-dimensional spatial coordinates are calculated by using the through-positions of the rings and markers of the identification part, which are seen through on the X-ray fluoroscopy image, and thus the second reality three-dimensional spatial coordinates of the image of the medical device and three-dimensional spatial coordinates of the marker are determined, thereby obtaining the relative position of an internal portion of the medical device from the three-dimensional spatial coordinates of the markers.

33. The system of claim 32, wherein the second reality three-dimensional spatial coordinates are calculated by using position information of the identification part, or position information and dimension information of the identification part.

34. The system of claim 19, wherein the imaging unit includes a plurality of cameras, the three-dimensional image of the periphery of the medical device being obtained using the plurality of cameras.

35. The system of claim 19, wherein the camera as the imaging unit includes an identification part.

36. The system of claim 19, wherein the imaging unit is an ultrasonic probe.

37. The system of claim 36, wherein the ultrasonic probe as the imaging unit includes an identification part.

38. The system of claim 19, wherein the three-dimensional image of the human body and the three-dimensional image of the periphery of the medical device are different kinds of images.

39. The system of claim 19, further comprising a processor for calculating a three-dimensional image of a periodic-mobility human body part, which has periodic mobility and generates signals linked with the periodic mobility, and fourth reality spatial coordinates thereof, wherein the second processor produces a complex reality three-dimensional image by using the first reality three-dimensional spatial coordinates, the second reality three-dimensional spatial coordinates, the third reality three-dimensional spatial coordinates, and the fourth reality spatial coordinates.

* * * * *